(12) United States Patent
Flohr et al.

(10) Patent No.: US 6,872,833 B2
(45) Date of Patent: Mar. 29, 2005

(54) ADENOSINE RECEPTOR LIGANDS

(75) Inventors: Alexander Flohr, Basel (CH); Roger David Norcross, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/812,736

(22) Filed: Mar. 30, 2004

(65) Prior Publication Data
US 2004/0204584 A1 Oct. 14, 2004

(30) Foreign Application Priority Data
Apr. 14, 2003 (EP) .............................. 03008038

(51) Int. Cl.⁷ .................. C07D 285/00; C07D 417/00; C07D 513/00
(52) U.S. Cl. ..................................... 548/123
(58) Field of Search ........................ 548/123

(56) References Cited

U.S. PATENT DOCUMENTS 6,521,754 B2 * 2/2003 Alanine et al. ............. 544/129

FOREIGN PATENT DOCUMENTS

| WO | WO 01/97786 A2 | 12/2001 |
| WO | WO 03/043636 A1 | 5/2003 |
| WO | WO 03/053961 A1 | 7/2003 |

\* cited by examiner

*Primary Examiner*—Alton Pryor
(74) *Attorney, Agent, or Firm*—George W. Johnston; Patricia S. Rocha-Tramaloni; Bernard Lau

(57) ABSTRACT

The present invention relates to compounds of the general formula I

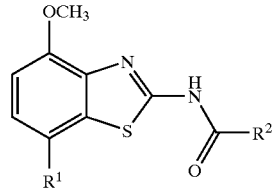

wherein $R^1$, $R^2$, R', R", n, m and o are defined herein, or a pharmaceutically acceptable salt thereof.

It has been found that the compounds of general formula I are adenosine receptor ligands with a good affinity to the $A_{2A}$-receptor and a high selectivity to the $A_1$- and $A_3$ receptors. These compounds have useful pharmacological activities.

25 Claims, No Drawings

ADENOSINE RECEPTOR LIGANDS

FIELD OF THE INVENTION

The present invention relates to novel adenosine receptor ligands of formula I

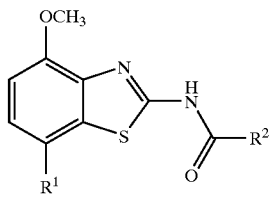

wherein $R^1$, $R^2$, R', R", n, m, and o are described hereinbelow. These ligands (compounds) have a good affinity to the $A_{2A}$-receptor and a high selectivity to $A_1$- and $A_3$-receptors. These compounds are useful, inter alia, in treatment of Alzheimer's disease, depression, Parkinson's disease and ADHD.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptores for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cydase, leading to an increase in cellular cAMP levels. It is known that the $A_1$ receptor system include the activation of phospholipase C and modulation of both potassium and calcium ion channels. The $A_3$ subtype, in addition to its association with adenylate cydase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes are to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioural state and (patho)physiological conditions. Under conditions of increased demand and decreased availability of energy (such as hypoxia, hypoglycemia, and/or excessive neuronal activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents.

Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyperactivity disorder).

An important role for adenosine in the cardiovascular system is as a cardioprotective agent. Levels of endogenous adenosine increase in-response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors. These include Bioorganic & Medicinal Chemistry, 6, (1998), 619–641, Bioorganic & Medicinal Chemistry, 6, (1998), 707–719, J. Med. Chem., (1998), 41, 2835–2845, J. Med. Chem., (1998), 41, 3186–3201, J. Med. Chem., (1998), 41, 2126–2133, J. Med. Chem., (1999), 42,706–721, J. Med. Chem., (1996), 39, 1164–1171, Arch. Pharm. Med. Chem., 332, 39–41, (1999), Am. J. Physiol., 276, H1113–1116, (1999) and Naunyn Schmied, Arch. Pharmacol. 362, 375–381, (2000).

SUMMARY OF THE INVENTION

An aspect of the present invention is directed to the compounds of formula I:

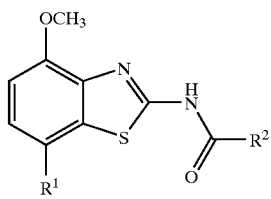

I wherein
$R^1$ is selected from (RS)-[1,4]dioxan-2-yl-, (R)-[1,4]dioxan-2-yl-, and (S)-[1,4]dioxan-2-yl-;
$R^2$ is
a)
—$(CH_2)_n$-pyridin-2, 3 or 4-yl, or
—$(CH_2)_n$-pyridin-2, 3 or 4-yl substituted by
-lower alkyl,
—$(CH_2)_m$—O-lower alkyl,
—$(CH_2)_m$NR'R",
—$(CH_2)_m$morpholinyl,
—$(CH_2)_m$-pyrrolidin-1-yl,
—$(CH_2)_m$-piperidine-1-yl,
—$(CH_2)_m$-piperidine-1-yl substituted by hydroxy,
—$(CH_2)_m$—O—$(CH_2)_o$—$CF_3$,
—$(CH_2)_n$—O—$(CH_2)_m$-cycloalkyl,
—$(CH_2)_m$—O—$(CH_2)_o$—O-lower alkyl,
—$(CH_2)_m$—O—$(CH_2)_o$-2-oxo-pyrrolidin-1-yl,
—$(CH_2)_m$—O-tetrahydropyran-4-yl,
—$(CH_2)_m$—O—$(CH_2)_o$-morpholinyl,
-di-hydropyran-4-yl,
-tetra-hydropyran-4-yl,
-azetidin-1-yl, or
-azetidin-1-yl substituted by halogen, lower alkoxy or hydroxy, or
b)
—$(CH_2)_n$-piperidine-1-yl, or
—$(CH_2)_n$-piperidine-1-yl substituted by one or two substituents selected from
-hydroxy, -hydroxy-lower alkyl, -lower alkyl and
—$(CH_2)_m$—O-lower alkyl; or
c)
—$(CH_2)_n$-phenyl, unsubstituted or mono-or di-substituted by
-halogen,
-lower alkyl,
-lower alkoxy, or
—$(CH_2)_n$—NR'R"; or
d)
-benzo[1.3]dioxol-5-yl;
—$(CH_2)_n$-morpholinyl;
—$(CH_2)_n$-tetrahydropyran-4-yl;
—$(CH_2)_n$—O-lower alkyl;
—$(CH_2)_n$-cycloalkyl;
—$(CH_2)_n$—C(O)—NR'R";
—$(CH_2)_n$-2-oxo-pyrrolidin-1-yl;
—$(CH_2)_n$NR'R";
-2-oxa-5-aza-bicyclo[2.2.1]heptane-5-yl; or
-1-oxa-8-aza-spiro[4.5]decane-8-yl;
R' and R" are each independently selected from lower alkyl; —$(CH_2)_o$—O-lower alkyl; cycloalkyl; lower alkyl substituted by one or two substituents selected from hydroxy and lower alkyl; —$(CH_2)_o$—O-lower alkyl substituted by one or two substituents selected from hydroxy and lower alkyl; and cycloalkyl substituted by one or two substituents selected from hydroxy and lower alkyl;
n is 0, 1, 2 or 3;
m is 0 or 1; and
o is 1 or 2;
or a pharmaceutically acceptable salt thereof.

Other embodiments of the invention are directed to methods of manufacture of compounds of formula I, pharmaceutical compositions containing a compound of formula I, and a pharmaceutically acceptable salt thereof, as well as a method of controlling or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse comprising administering to a patient a therapeutically effective amount of compound of formula I or a pharmaceutically acceptable salt thereof.

Furthermore, compounds of the present invention are useful as sedatives, muscle relaxants, antipsychotics, antiepileptics, anticonvulsants and cardiaprotective agents for disorders such as coronary artery disease and heart failure. Preferred indications in accordance with the present invention are those that depend on $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

As used herein, the term "lower alkyl" refers to a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" refers to chlorine, iodine, fluorine and bromine.

The term "cycloalkyl" refers to a saturated carbocyclic group, containing 3–7 carbon atoms.

The term "lower alkoxy" refers to a group wherein the alkyl residues is as defined above, and which is attached via an oxygen atom.

The term "pharmaceutically acceptable acid addition salts" refers to salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" refers to an amount of at least one compound of formula I, or a pharmaceutically acceptable salt thereof, that modulates adenosine.

Preferred compounds of formula I are

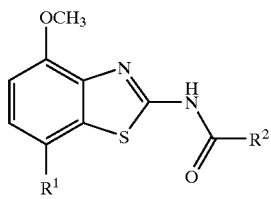

wherein $R^1$ is selected from (RS)-[1,4]dioxan-2-yl-, (R)-[1,4]dioxan-2-yl-, and (S)-[1,4]dioxan-2-yl-;

$R^2$ is a)
—$(CH_2)_n$-pyridin-2, 3 or 4-yl, or
—$(CH_2)_n$-pyridin-2, 3 or 4-yl substituted by
-lower alkyl,
—$(CH_2)_m$—O-lower alkyl
—$(CH_2)_m$NR'R'',
—$(CH_2)_m$morpholinyl,
—$(CH_2)_m$-pyrrolidin-1-yl,
—$(CH_2)_m$-piperidine-1-yl,
—$(CH_2)_m$-piperidine-1-yl substituted by hydroxy,
—$(CH_2)_m$—O—$(CH_2)_o$—$CF_3$,
—$(CH_2)_n$—O—$(CH_2)_m$-cycloalkyl,
—$(CH_2)_m$—O—$(CH_2)_o$—O-lower alkyl,
—$(CH_2)_m$—O—$(CH_2)_o$-2-oxo-pyrrolidin-1-yl,
—$(CH_2)_m$—O-tetrahydropyran-4-yl,
—$(CH_2)_m$—O—$(CH_2)_o$-morpholinyl,
-di-hydropyran-4-yl,
-tetra-hydropyran-4-yl,
-azetidin-1-yl, or
-azetidin-1-yl substituted by halogen, lower alkoxy or hydroxy, or b)
—$(CH_2)_n$-piperidine-1-yl, or
—$(CH_2)_n$-piperidine-1-yl substituted by one or two substituents selected from
-hydroxy, -hydroxy-lower alkyl, -lower alkyl and
—$(CH_2)_m$—O-lower alkyl; or c)
—$(CH_2)_n$-phenyl, or
—$(CH_2)_n$-phenyl substituted by one or two substitents selected from -halogen, -lower alkyl, -lower alkoxy and —$(CH_2)_n$—NR'R''; or d)
-benzo[1.3]dioxol-5-yl;
—$(CH_2)_n$-morpholinyl;
—$(CH_2)_n$-tetrahydropyran-4-yl;
—$(CH_2)_n$—O-lower alkyl;
—$(CH_2)_n$-cycloalkyl;
—$(CH_2)_n$—C(O)—NR'R'';
—$(CH_2)_n$-2-oxo-pyrrolidin-1-yl;
—$(CH_2)_n$NR'R'';
-2-oxa-5-aza-bicyclo[2.2.1]heptane-5-yl; or
-1-oxa-8-aza-spiro[4.5]decane-8-yl; and R' and R'' are each independently selected from lower alkyl; —$(CH_2)_o$—O-lower alkyl; cycloalkyl; lower alkyl substituted by one or two substituents selected from hydroxy and lower alkyl; —$(CH_2)_o$—O-lower alkyl substituted by one or two substituents selected from hydroxy and lower alkyl; and cycloalkyl substituted by one or two substituents selected from hydroxy and lower alkyl; and n is 0, 1, 2 or 3;
m is 0 or 1; and
o is 1 or 2;

or a pharmaceutically acceptable salt thereof.

Another preferred set of compounds of formula I of the present invention includes compounds where $R^2$ is substituted —$(CH_2)_n$-pyridin-4-yl, wherein the substituents are selected from the group consisting of methyl, morpholinyl, azetidin-1-yl, 3-fluoro-azetidin-1-yl, 3-methoxy-azetidin-1-yl, 3-hydroxy-azetidin-1-yl and —O—$(CH_2)_2$-morpholinyl.

Examples of this group of compounds include:

(+)-N-(7-[1,4]dioxan-2-yl-4-methoxy-benzothiazol-2-yl)-2-methyl-isonicotinamide,
(+)-N-(7-[1,4]dioxan-2-yl-4-methoxy-benzothiazol-2-yl)-2-morpholin-4-yl-isonicotinamide,
(+)-2-azetidin-1-yl-N-(7-[1,4]dioxan-2-yl-4-methoxy-benzothiazol-2-yl)-isonicotinamide,
(+)-N-(7-[1,4]dioxan-2-yl-4-methoxy-benzothiazol-2-yl)-2-(3-fluoro-azetidin-1-yl)-isonicotinamide,
(+)-N-(7-[1,4]dioxan-2-yl-4-methoxy-benzothiazol-2-yl)-2-(3-methoxy-azetidin-1-yl)-isonicotinamide,
(+)-N-(7-[1,4]dioxan-2-yl-4-methoxy-benzothiazol-2-yl)-2-(3-hydroxy-azetidin-1-yl)-isonicotinamide, and
(+)-N-(7-[1,4]dioxan-2-yl-4-methoxy-benzothiazol-2-yl)-2-(2-morpholin-4-yl-ethoxy)-isonicotinamide.

Another preferred set of compounds of formula I of the present invention includes those wherein $R^2$ is substituted —$(CH_2)_n$-pyridin-3-yl, substituted by methoxy, for example, the compound (+)-N-(7-[1,4]dioxan-2-yl-4-methoxy-benzothiazol-2-yl)-5-methoxy-nicotinamide.

Another preferred set of compounds of formula I of the present invention includes those wherein $R^2$ is substituted —$(CH_2)_n$-pyridin-2-yl.

Another preferred set of compounds of formula I of the present invention includes those wherein $R^2$ is unsubstituted —$(CH_2)_n$-pyridin-2, 3 or 4-yl.

Another preferred set of compounds of formula I includes those, wherein $R^2$ is mono- or di-substituted —$(CH_2)_n$-phenyl, and wherein the substituents are fluoro, mono- or di-methoxy or methyl groups. Examples include:

(+)-N-(7-[1,4]dioxan-2-yl-4-methoxy-benzothiazol-2-yl)-4-fluoro-benzamide,
(+)-N-(7-[1,4]dioxan-2-yl-4-methoxy-benzothiazol-2-yl)-4-methoxy-benzamide,
(+)-N-(7-[1,4]dioxan-2-yl-4-methoxy-benzothiazol-2-yl)-4-methyl-benzamide and
(+)-N-(7-[1,4]dioxan-2-yl-4-methoxy-benzothiazol-2-yl)-3-methoxy-benzamide.

Another preferred set of compounds of formula I includes those, wherein $R^2$ is unsubstituted —$(CH_2)_n$-phenyl.

Another preferred set of compounds of formula I includes those wherein $R^2$ is the benzo[1.3]dioxol-5-yl group, which includes compound (+)-benzo[1,3]dioxole-5-carboxylic acid (7-[1,4]dioxan-2-yl-4-methoxy-benzothiazol-2-yl)-amide.

Another preferred set of compounds of formula I includes those wherein $R^2$ is —$(CH_2)_n$-morpholinyl, —$(CH_2)_n$-tetrahydropyran-4-yl, —$(CH_2)_n$—O-lower alkyl, —$(CH_2)_n$-cycloalkyl, —$(CH_2)_n$—C(O)—NR'R", —$(CH_2)_n$-2-oxo-pyrrolidin-1-yl, —$(CH_2)_n$NR'R", -2-oxa-5-aza-bicyclo[2.2.1]heptane-5-yl and -1-oxa-8-aza-spiro[4.5]decane-8-yl.

The present compounds of formula I and their pharmaceutically acceptable salts can be prepared by methods known in the art, for example:

a) reacting a compound of formula 5

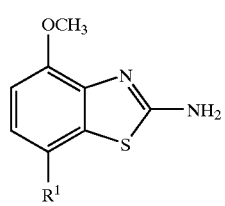

(5)

with a compound of formula

 (6)

or with a compound of formula

 (7)

to form a compound of formula I

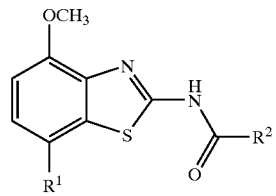

I wherein $R^1$ is as defined above, or b) reacting a compound of formula 8

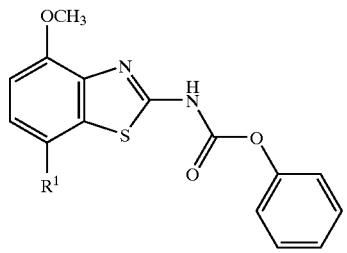

(8)

with a compound of formula

 (9)

to form a compound of formula I

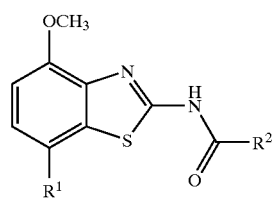

I wherein $R^1$ is as defined above, or c) separating a racemic compound of formula I into its (R)- and (S)-enantiomers, or d) modifying the substituent $R^2$ within the definitions given above, and if desired, converting the compounds obtained into pharmaceutically acceptable salts.

The compounds of formula I may be prepared in accordance with process variants a)–d) and with the following schemes I and II.

Preparation of Compounds of Formula I

One method for preparing compounds of formula I is from compounds of formula (5), the preparation of which is shown in reaction scheme 1 below.

Scheme 1
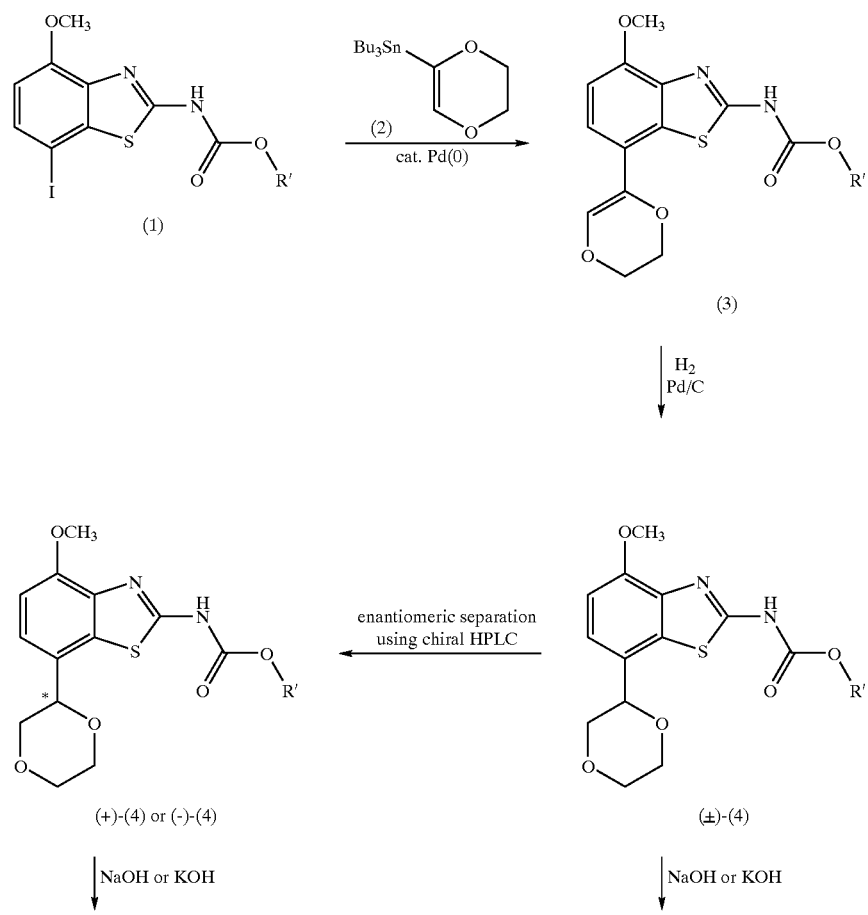
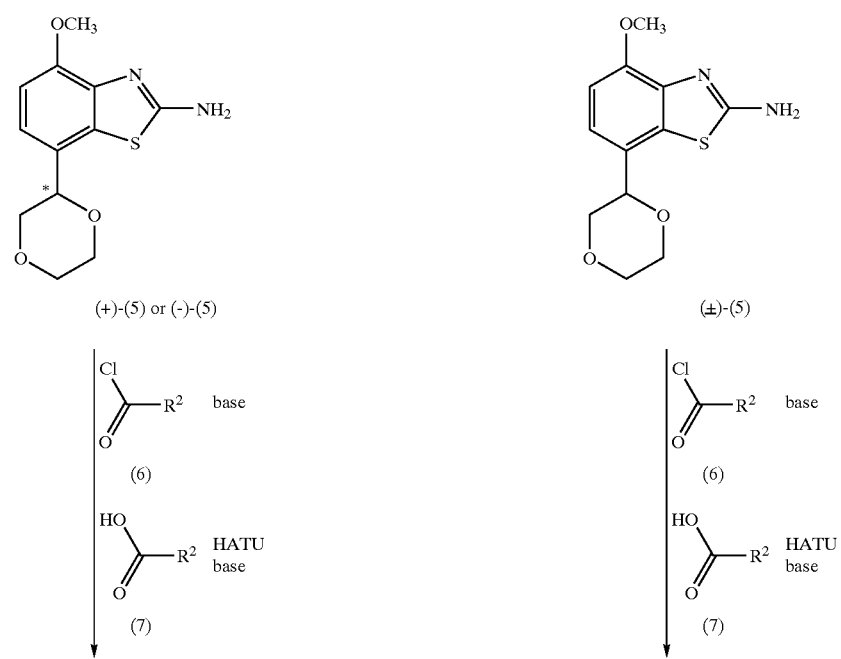

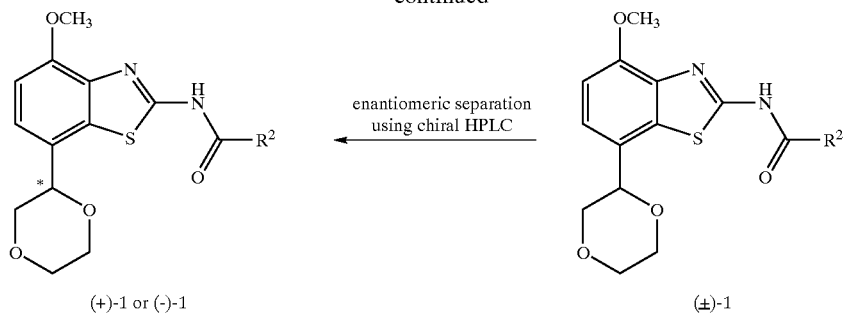

(+)-1 or (−)-1              (±)-1

\* indicates compounds are configurationally pure at the indicated stereogenic centre wherein R' is methyl or ethyl, $R^2$ is as defined above, with the exception of cases where $R^2$ is attached by an atom other than C, and HATU is O-(7-azabenzotriazol-1-yl)-N,N,N',N'-tetramethyluronium hexafluorophosphate.

Preparation of Compounds of Formula (3)

The starting 7-iodo-benzothiazole derivatives of formula (1) may be prepared according to methods disclosed in EP 00113219.0. The starting tributylstannane compound of formula (2) may be prepared according to methods well known in the art.

The 7-iodo-benzothiazole derivative of formula (1) is reacted with an excess of the tributylstannane compound of formula (2) in an organic solvent, preferably dioxane, containing a palladium catalyst, preferably bis(dibenzylideneacetone)palladium(0), and a catalytic amount of a phosphine ligand, preferably trifurylphosphine. The reaction is carried out at elevated temperature, preferably about 100° C., for about 2–24 hours, preferably about 16 hours. The product of formula (3) is isolated by conventional means, and preferably purified by means of chromatography or recrystallisation.

Preparation of Compounds of Formula (4) in Racemic Form

Compounds of formula (4) may be prepared in racemic form by hydrogenation of compounds of formula (3) in the presence of a hydrogenation catalyst, preferably 10% palladium on charcoal. These reactions are preferably carried out in a mixture of dioxane and acetic acid, at room temperature and at a pressure of one atmosphere or above, preferably at 10 bar, for 16–72 hours, preferably about 24 hours. The racemic product of formula (±)-(4) is isolated by conventional means, and preferably purified by means of chromatography or recrystallization.

Preparation of Compound of Formula (5) in Racemic Form

One method of preparation of the compound of formula (5) in racemic form is by treatment of a racemic compound of formula (±)-(4) with an excess of sodium hydroxide or potassium hydroxide in an aqueous solvent, preferably aqueous ethylene glycol. The reaction is carried out at elevated temperature, preferably about 100° C., for about 1–16 hours, preferably about 16 hours. The racemic product of formula (±)-(5) is isolated by conventional means, and preferably purified by means of chromatography or recrystallization.

Preparation of Compounds of Formula I in Racemic Form

One method for preparing compounds of formula I in racemic form is by treating a racemic compound of formula (±)-(5) with a slight excess of an appropriate acyl chloride of formula (6), which may be commercially available or maybe prepared by methods well known in the art. The reaction is carried out in a non-protic organic solvent preferably a mixture of dichloromethane and tetrahydrofuran, containing a base, preferably N-ethyldiisopropylamine or triethylamine, at room temperature for 2–48 hours, preferably 24 hours. The racemic product of formula (±)-I is isolated by conventional means, and preferably purified by means of chromatography or recrystallization.

Alternative Preparation of Compounds of Formula I in Racemic Form

An alternative method for preparing compounds of formula I in racemic form involves treating of an appropriate carboxylic acid of formula (7) with a stoichiometric equivalent of a peptide-coupling reagent, preferably O-(7-azabenzotriazol-1-yl)-N,N,N',N'-tetramethyluronium hexafluorophosphate (HATU), in an ethereal solvent, preferably tetrahydrofuran, containing a base, preferably N-ethyldiisopropylamine, at room temperature for 1–2 hours, preferably 1 hour. This mixture is then treated with a racemic compound of formula (±)-(5) at room temperature for 16–24 hours, preferably 16 hours. The product of Formula (±)-I is isolated by conventional means, and preferably purified by means of chromatography or recrystallization.

Preparation of Compounds of Formula I in Enantiomerically Pure Form

One method for preparing compounds of formula I in enantiomerically pure form is by chiral separation of the corresponding racemic compounds of formula I. The chiral separation may be carried out by high performance liquid chromatography (HPLC) using a chiral stationary phase, preferably Chiralpak AD. Following a successful chiral separation, the dextrorotatory enantiomer of formula (+)-I and laevororotatory enantiomer of formula (−)-I are isolated as separate chromatographic fractions.

Alternative Preparation of Compounds of Formula I in Enantiomerically Pure Form

An alternative method for preparing compounds of formula I in enantiomerically pure form is by starting from an enantiomerically pure form of the intermediate compound of formula (5), which may in turn be prepared by starting from an enantiomerically pure form of the intermediate compound of formula (4). One method for preparing compounds of formula (4) in enantiomerically pure form is by chiral separation of the corresponding racemic compounds of formula (4). The chiral separation may be carried out by high performance liquid chromatography (HPLC) using a chiral stationary phase, preferably Chiralpak AD. Following a successful chiral separation, the dextrorotatory enantiomer of formula (+)-(4) and levorotatory enantiomer of formula (−)-(4) are isolated as separate chromatographic fractions.

The enantiomerically pure compounds of formula (4) may be converted to enantiomerically pure compound of formula (5) and then to enantiomerically pure compounds of formula I using the same methods already described for the analogous transformation of the racemic compounds (±)-(4) to (±)-I via (±)-(5).

Alternative Preparation of Compounds of Formula I

An alternative method of preparation of compounds of formula I is from a compound of formula (8), the preparation of which is shown in reaction scheme 2 below.

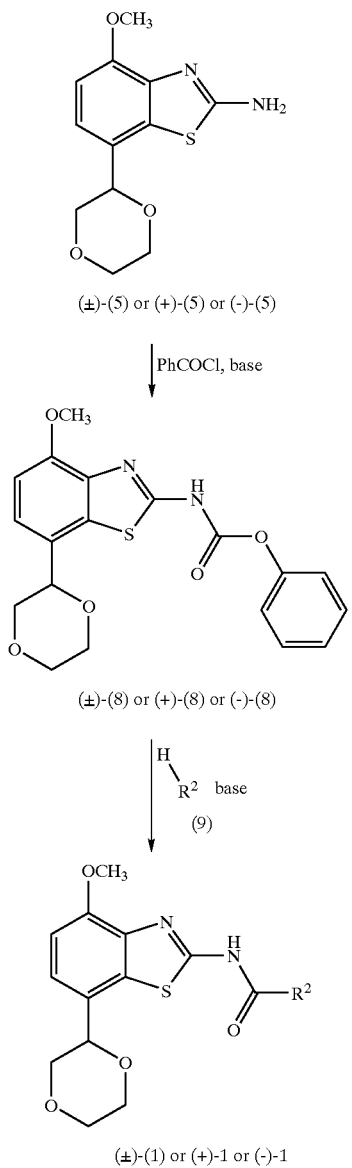

wherein $R^2$ is piperidine-1-yl, unsubstituted or mono- or di-substituted by hydroxy, hydroxy-lower alkyl, lower alkyl or —$(CH_2)_m$—O-lower alkyl; morpholinyl; -1-oxa-8-aza-spiro[4.5]decane-8-yl; or is —NR'R", where R' and R" are independently from each other lower alkyl, —$(CH_2)_o$—O-lower alkyl, cycloalkyl, optionally mono- or di-substituted by hydroxy or lower alkyl; m is 0 or 1; and o is 1 or 2.

Preparation of Compound of Formula (8)

One method of preparation of the compound of formula (8) is by treatment of the compound of formula (5) with a slight excess of phenyl chloroformate in an organic solvent, preferably dichloromethane, in the presence of a base, preferably pyridine. The reaction is carried out a temperature between 0° C. and room temperature for about 1–16 hours, preferably about 16 hours. The product of formula (8) is isolated by conventional means, and preferably purified by means of chromatography or recrystallization.

The compound of formula (8) may be prepared in either racemic or enantiomerically pure form, depending on whether the starting material of formula (5) is racemic or enantiomerically pure.

Preparation of Compounds of Formula I

One method for preparing compounds of formula I is by treating the compound of formula (8) with an excess of an appropriate amine of formula (9), which may be commercially available or may be prepared by methods well known in the art. The reaction is carried out in an organic solvent, preferably chloroform, containing a base, preferably N-ethyldiisopropylamine or pyridine, at an elevated temperature, preferably around 50° C., for 2–24 hours, preferably 16 hours. The product of formula I is isolated by conventional means, and preferably purified by means of chromatography or recrystallization.

The compound of formula I may be prepared in either racemic or enantiomerically pure form, depending on whether the starting material of formula (8) is racemic or enantiomerically pure.

Conversion of Compounds of Formula I to Other Compounds of Formula I Bearing a Modified $R^2$ Substituent In cases where the compound of formula I contains an $R^2$ substituent bearing a chemically reactive functional group, for instance when $R^2$ contains benzylic halide functionality or 2-halo-pyridyl functionality, the compound of formula I may be converted to another compound of formula I having a modified $R^2$ substituent, by reactions involving the reactive functionality contained in the original $R^2$ substituent. Such transformations may be carried out according to methods well known in the art and a number of the examples below provide certain specific examples. For instance, compounds of formula I containing $R^2$ substituents bearing benzylic halide functionality or 2-halo-pyridyl functionality may be reacted with nucleophilic alcohol or amine reagents to afford compounds of formula I containing $R^2$ substituents bearing, respectively, benzylic ether or benzylic amine functional groups, or pyridyl-2-yl-ether or pyridyl-2-yl-amino functional groups.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. The Preparation and Examples sections below provide specific illustrations of suitable separation and isolation procedures. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of formula I may be converted to a corresponding salt.

The conversion is accomplished by treatment with at least a stoichiometric amount of an appropriate acid, such as hydrochloric acid, hydrobromic acid, sulfuric acid, nitric acid, phosphoric acid and the like; and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable salts possess valuable pharmacological properties. Specifically, it has been found that the compounds of the present invention are adenosine receptor ligands and possess a high affinity towards the adenosine $A_{2A}$ receptor and a good selectivity towards $A_1$ and $A_3$ receptors. The compounds were investigated in accordance with the tests given hereinafter.

Human Adenosine $A_1$ Receptor

The human adenosine $A_1$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-DPCPX (([propyl-$^3$H]8-cyclopentyl-1,3-dipropyxanthine); 0.6 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand was determined using a Packard Topcount scintillation counter. $IC_{50}$ values were calculated using a non-linear curve fitting program and Ki values calculated using the Cheng-Prussoff equation.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

It has been shown that compounds of formula I have a good affinity to the $A_{2A}$ receptor and a high selectivity toward the $A_1$ and $A_3$ receptor. The $hA_2$ pKi of the present compounds is in the range of 7.11–9.38. The preferred compounds show a $hA_2$ pKi>9.0.

| Example No. | $hA_2$ (pKi) | Selectivity to $hA_1$ |
|---|---|---|
| 5 | 8.84 | 1421 |
| 6 | 8.88 | 1582 |
| 14 | 8.92 | 1828 |
| 15 | 9.02 | 1758 |
| 16 | 9.08 | 1005 |
| 17 | 9.17 | 3874 |
| 18 | 9.01 | 7378 |
| 29 | 8.97 | 2850 |
| 30 | 9.05 | 6138 |
| 31 | 8.91 | 2718 |
| 32 | 9.19 | 5404 |
| 33 | 9.15 | 1238 |
| 34 | 9.38 | 4503 |
| 36 | 9.27 | 1411 |
| 37 | 9.14 | 10082 |
| 39 | 8.97 | 674 |
| 49 | 9.07 | 2319 |
| 52 | 9.30 | 3141 |
| 53 | 9.08 | 8832 |

The compounds of formula I and the pharmaceutically acceptable salts of the compounds of formula I can be used as medicaments, e.g., in the form of pharmaceutical preparations. The pharmaceutical preparations can be administered orally, e.g., in the form of tablets, coated tablets, dragées, hard and soft gelatine capsules, solutions, emulsions or suspensions. The administration can, however, also be effected rectally, e.g., in the form of suppositories, parenterally, e.g., in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

Highly preferred indications in accordance with the present invention are those, which include disorders of the central nervous system, for example, the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4 | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLES

The following preparation and examples illustrate the invention but are not intended to limit its scope.

Example 1

(±)-N-(7-[1,4]Dioxan-2-yl-4-methoxy-benzothiazol-2-yl)-2-methyl-isonicotinamide a) [7-(5,6-Dihydro-[1,4]dioxin-2-yl)-4-methoxy-benzothiazol-2-yl]-carbamic acid methyl ester To a stirred solution of 13.0 g (35.7 mmol) (7-iodo-4-methoxy-benzothiazol-2-yl)-carbamic acid methyl ester in 200 ml dioxane were added 20.1 g (53.6 mmol) tributyl-(5,6-dihydro-[1,4]dioxin-2-yl)-stannane, 616 mg (1.07 mmol) bis(dibenzylideneacetone)palladium, 1.33 g (5.71 mmol) trifurylphosphine and 7.46 ml (53.6 mmol) triethylamine. The mixture was heated at 100° C. for 16 h and then poured onto water and extracted three times with ethyl acetate. The combined organic phases were dried over sodium sulfate and concentrated in vacuo. Flash chromatography (1/4–1/2 acetone/hexane) followed by trituration in ether afforded 5.20 g (45%) [7-(5,6-dihydro-[1,4]dioxin-2-yl)-4-methoxy-benzothiazol-2-yl]-carbamic acid methyl ester as a white solid. ES-MS m/e (%): 323 (M+H$^+$, 100).

b) (±)-(7-[1,4]Dioxan-2-yl-4-methoxy-benzothiazol-2-yl)-carbamic acid methyl ester To a stirred solution of 4.90 g (15.2 mmol) [7-(5,6-dihydro-[1,4]dioxin-2-yl)-4-methoxy-benzothiazol-2-yl]-carbamic acid methyl ester in 250 ml dioxane and 5 ml acetic acid was added 4.9 g of 10% palladium on charcoal and the mixture was then stirred for 24 h at room temperature under a 10 bar atmosphere of hydrogen. The mixture was then filtered, washing with dioxane, and the filtrate concentrated in vacuo. Trituration in acetone afforded 3.90 g (79%) (±)-(7-[1,4]dioxan-2-yl-4-methoxy-benzothiazol-2-yl)-carbamic acid methyl ester as a white solid. ES-MS m/e (%): 325 (M+H$^+$, 100).

c) (±)-7-[1,4]Dioxan-2-yl-4-methoxy-benzothiazol-2-ylamine

To a stirred solution of 1.10 g (3.39 mmol) (±)-(7-[1,4]dioxan-2-yl-4-methoxy-benzothiazol-2-yl)-carbamic acid methyl ester in 50 ml dioxane and 50 ml ethylene glycol was added 100 ml of a 5 N aq. sodium hydroxide solution and the mixture was heated at 100° C. for 16 h. After cooling to room temperature the mixture was poured onto water and extracted three times with ethyl acetate. The combined organic phases were washed with brine, then dried over sodium sulfate and concentrated in vacuo. Trituration in methanol afforded 0.66 g (73%) (±)-7-[1,4]dioxan-2-yl-4-methoxy-benzothiazol-2-ylamine as a white solid. ES-MS m/e (%): 267 (M+H$^+$, 100).

d) (±)-N-(7-[1,4]Dioxan-2-yl-4-methoxy-benzothiazol-2-yl)-2-methyl-isonicotinamide To a stirred solution of 85 mg (0.49 mmol) 2-methyl-isonicotinic acid hydrochloride in 10 ml THF were added 214 mg (0.56 mmol) HATU and 0.16 ml (0.94 mmol) N-ethyldiisopropylamine and stirring continued at room temperature for 1 h. 100 mg (0.38 mmol) (±)-7-[1,4]dioxan-2-yl-4-methoxy-benzothiazol-2-ylamine was then added and stirring continued at room temperature for 24 h. The reaction mixture was then poured into saturated aqueous sodium bicarbonate solution and extracted three times with ethyl acetate. The combined organic phases were dried over sodium sulfate and concentrated in vacuo. Trituration in ether afforded 95 mg (66%) (±)-N-(7-[1,4]dioxan-2-yl-4-methoxy-benzothiazol-2-yl)-2-methyl-isonicotinamide as a white solid. ES-MS m/e (%): 386 (M+H$^+$, 100).

In an analogous manner there was obtained:

Example 2

(±)-N-(7-[1,4]Dioxan-2-yl-4-methoxy-benzothiazol-2-yl)-4-fluoro-benzamide

From 4-fluoro-benzoic acid, HATU and N-ethyldiisopropylamine in THF, then treatment with (±)-7-[1,4]dioxan-2-yl-4-methoxy-benzothiazol-2-ylamine. ES-MS m/e (%): 389 (M+H$^+$, 100).

Example 3

(±)-N-(7-[1,4]Dioxan-2-yl-4-methoxy-benzothiazol-2-yl)-2-morpholin-4-yl-isonicotinamide a) (±)-2-Bromo-N-(7-[1,4]dioxan-2-yl-4-methoxy-benzothiazol-2-yl)-isonicotinamide To a stirred solution of 296 mg (1.46 mmol) 2-bromo-isonicotinic acid in 10 ml THF were added 642 mg (1.69 mmol) HATU and 0.29 ml (1.69 mmol) N-ethyldiisopropylamine and stirring continued at room temperature for 1 h. 300 mg (1.13 mmol) (±)-7-[1,4]dioxan-2-yl-4-methoxy-benzothiazol-2-ylamine was then added and stirring continued at room temperature for 24 h. The reaction mixture was then poured into saturated aqueous sodium bicarbonate solution and extracted three times with ethyl acetate. The combined organic phases were dried over sodium sulfate and concentrated in vacuo. Trituration in ether afforded 370 mg (73%) (±)-2-bromo-N-(7-[1,4]dioxan-2-yl-4-methoxy-benzothiazol-2-yl)-isonicotinamide as a light yellow solid. ES-MS m/e (%):452 (M{$^{81}$Br}+H$^+$, 100), 450 (M{$^{79}$Br}+H$^+$, 95).

b) (±)-N-(7-[1,4]Dioxan-2-yl-4-methoxy-benzothiazol-2-yl)-2-morpholin-4-yl-isonicotinamide A stirred suspension of 150 mg (0.33 mmol) (±)-2-bromo-N-(7-[1,4]dioxan-2-yl-4-methoxy-benzothiazol-2-yl)-isonicotinamide, 217 mg (0.67 mmol) cesium carbonate and a few crystals of 2,6-di-tert-butyl-p-cresol in 2.90 ml (3.33 mmol) morpholine in a thick-walled glass pressure tube fitted with a teflon cap was heated at 140° C. for 24 h. The reaction mixture was then cooled to room temperature and poured onto water. The mixture was extracted three times with ethyl acetate, and the combined organic phases were dried over sodium sulfate and concentrated in vacuo. Flash chromatography (ethyl acetate) followed by trituration in ether afforded 65 mg (43%) (±)-N-(7-[1,4]dioxan-2-yl-4-methoxy-benzothiazol-2-yl)-2-morpholin-4-yl-isonicotinamide as a light yellow solid. ES-MS m/e (%): 457 (M+H$^+$, 100).

Analogously to Example 1 there was obtained

Example 4

(±)-N-(7-[1,4]Dioxan-2-yl-4-methoxy-benzothiazol-2-yl)-2-methoxy-isonicotinamide From 2-methoxy-isonicotinic acid hydrochloride, HATU and N-ethyldiisopropylamine in THF, then treatment with (±)-7-[1,4]dioxan-2-yl-4-methoxy-benzothiazol-2-ylamine. ES-MS m/e (%): 402 (M+H$^+$, 100).

Example 5

(±)-2-(3,6-Dihydro-2H-pyran-4-yl)-N-(7-[1,4]dioxan-2-yl-4-methoxy-benzothiazol-2-yl)-isonicotinamide To a stirred solution of 180 mg (0.40 mmol) (±)-2-bromo-N-(7-[1,4]dioxan-2-yl-4-methoxy-benzothiazol-2-yl)-isonicotinamide in 10 ml DMF were added 298 mg (0.80 mmol) tributyl-(3,6-dihydro-2H-pyran-4-yl)-stannane, 34 mg (0.05 mmol) bis(triphenylphosphine)palladium(II) chloride, 63 mg (0.24 mmol) triphenylphosphine, 136 mg (3.20 mmol) lithium chloride and a small spatula-end of 2,6-di-tert-butyl-4-methylphenol. The mixture was heated at 100° C. for 24 h and then concentrated in vacuo. Flash chromatography (ethyl acetate) afforded 140 mg (77%) (±)-2-(3,6-dihydro-2H-pyran-4-yl)-N-(7-[1,4]dioxan-2-yl-4-methoxy-benzothiazol-2-yl)-isonicotinamide as an off-white solid. ES-MS m/e (%): 454 (M+H$^+$, 100).

Example 6

(±)-N-(7-[1,4]Dioxan-2-yl-4-methoxy-benzothiazol-2-yl)-2-(tetrahydro-pyran-4-yl)-isonicotinamide To a stirred solution of 130 mg (0.29 mmol) (±)-2-(3,6-dihydro-2H-pyran-4-yl)-N-(7-[1,4]dioxan-2-yl-4-methoxy-benzothiazol-2-yl)-isonicotinamide in 10 ml methanol and 10 ml dichloromethane was added a spatula end of 10% palladium on charcoal and the mixture was then stirred for 16 h at room temperature under an atmosphere of hydrogen. The mixture was then filtered, washing with dichloromethane, and the filtrate concentrated in vacuo. Flash chromatography (2/49/49 methanol/dichloromethane/ethyl acetate) followed by trituration in ether afforded 60 mg (46%) (±)-N-(7-[1,4]dioxan-2-yl-4-methoxy-benzothiazol- 2-yl)-2-(tetrahydro-pyran-4-yl)-isonicotinamide as a white crystalline solid. ES-MS m/e (%): 456 (M+H⁺, 100).

Analogously to Example 1 there were obtained

Example 7
(±)-N-(7-[1,4]Dioxan-2-yl-4-methoxy-benzothiazol-2-yl)-2-isopropyl-isonicotinamide From 2-isopropyl-isonicotinic acid, HATU and N-ethyldiisopropylamine in THF, then treatment with (±)-7-[1,4]dioxan-2-yl-4-methoxy-benzothiazol-2-ylamine. ES-MS m/e (%): 414 (M+H⁺, 100).

Example 8
(±)-2-tert-Butyl-N-(7-[1,4]dioxan-2-yl-4-methoxy-benzothiazol-2-yl)-isonicotinamide From 2-tert-butyl-isonicotinic acid, HATU and N-ethyldiisopropylamine in THF, then treatment with (±)-7-[1,4]dioxan-2-yl-4-methoxy-benzothiazol-2-ylamine. ES-MS m/e (%): 428 (M+H⁺, 100).

Example 9
(±)-N-(7-[1,4]Dioxan-2-yl-methoxy-benzothiazol-2-yl)-2-phenyl-acetamide From phenylacetic acid, HATU and N-ethyldiisopropylamine in THF, then treatment with (±)-7-[1,4]dioxan-2-yl-4-methoxy-benzothiazol-2-ylamine. ES-MS m/e (%): 385 (M+H⁺, 100).

Example 10
(±)-N-(7-[1,4]Dioxan-2-yl-4-methoxy-benzothiazol-2-yl)-2-(6-methyl-pyridin-3-yl)-acetamide From (6-methyl-pyridin-3-yl)-acetic acid, HATU and N-ethyldiisopropylamine in THF, then treatment with (±)-7-[1,4]dioxan-2-yl-4-methoxy-benzothiazol-2-ylamine. ES-MS m/e (%): 400 (M+H⁺, 100).

Example 11
(±)-N-(7-[1,4]Dioxan-2-yl-4-methoxy-benzothiazol-2-yl)-2-pyridin-2-yl-acetamide From 2-pyridylacetic acid hydrochloride, HATU and N-ethyldiisopropylamine in THF, then treatment with (±)-7-[1,4]dioxan-2-yl-4-methoxy-benzothiazol-2-ylamine. ES-MS m/e (%): 386 (M+H⁺, 100).

Analogously to Example 3 there was obtained

Example 12
(±)-2-Azetidin-1-yl-N-(7-[1,4]dioxan-2-yl-4-methoxy-benzothiazol-2-yl)-isonicotinamide From (±)-2-bromo-N-(7-[1,4]dioxan-2-yl-4-methoxy-benzothiazol-2-yl)-isonicotinamide with cesium carbonate and azetidine. ES-MS m/e (%): 427 (M+H⁺, 100).

Example 13
(−)-N-(7-[1,4]Dioxan-2-yl-4-methoxy-benzothiazol-2-yl)-2-methoxy-isonicotinamide and Example 14
(+)-N-(7-[1,4]Dioxan-2-yl-4-methoxy-benzothiazol-2-yl)-2-methoxy-isonicotinamide 50 mg (±)-N-(7-[1,4]Dioxan-2-yl-4-methoxy-benzothiazol-2-yl)-2-methoxy-isonicotinamide was subjected to separation by chiral HPLC (stationary phase: Chiralpak AD; flow rate: 1 ml min⁻¹ at 30 bar; eluant: ethanol/heptane 1/4) to afford 18 mg (−)-N-(7-[1,4]dioxan-2-yl-4-methoxy-benzothiazol-2-yl)-2-methoxy-isonicotinamide having HPLC $R_t$=22.5 min, $[\alpha]_D^{20}$=−31.6° (c=0.81, CHCl₃), ES-MS m/e (%): 402 (M+H⁺, 100) and 18 mg (+)-N-(7-[1,4]dioxan-2-yl-4-methoxy-benzothiazol-2-yl)-2-methoxy-isonicotinamide having HPLC $R_t$=32.2 min, $[\alpha]_D^{20}$=+27.1° (c=1.02, CHCl₃), ES-MS m/e (%): 402 (M+H⁺, 100).

Example 15
(+)-N-(7-[1,4]Dioxan-2-yl-4-methoxy-benzothiazol-2-yl)-2-methyl-isonicotinamide a) [7-(5,6-Dihydro-[1,4]dioxin-2-yl)-4-methoxy-benzothiazol-2-yl]-carbamic acid ethyl ester To a stirred solution of 5.0 g (13.2 mmol) (7-iodo-4-methoxy-benzothiazol-2-yl)-carbamic acid ethyl ester in 60 ml dioxane were added 6.94 g (18.5 mmol) tributyl-(5,6-dihydro-[1,4]dioxin-2-yl)-stannane, 456 mg (0.79 mmol) bis(dibenzylideneacetone)palladium and 491 mg (2.12 mmol) trifurylphosphine. The mixture was heated at 100° C. for 3 h, then cooled to room temperature and concentrated in vacuo. Flash chromatography (5/95 acetone/dichloromethane) afforded 4.00 g (90%) [7-(5,6-dihydro-[1,4]dioxin-2-yl)-4-methoxy-benzothiazol-2-yl]-carbamic acid ethyl ester as a light yellow foam. ES-MS m/e (%): 337 (M+H⁺, 100).

b) (±)-(7-[1,4]Dioxan-2-yl-4-methoxy-benzothiazol-2-yl)-carbamic acid ethyl ester To a stirred solution of 12.0 g (35.7 mmol) [7-(5,6-dihydro-[1,4]dioxin-2-yl)-4-methoxy-benzothiazol-2-yl]-carbamic acid ethyl ester in 600 ml dioxane and 12 ml acetic acid was added 12 g of 10% palladium on charcoal and the mixture was then stirred for 48 h at room temperature under a 10 bar atmosphere of hydrogen. The mixture was then filtered, washing with dioxane, and the filtrate concentrated in vacuo. Flash chromatography (1/1 acetone/dichloromethane) followed by trituration in ether and hexane afforded 7.50 g (62%) (±)-(7-[1,4]dioxan-2-yl-4-methoxy-benzothiazol-2-yl)-carbamic acid ethyl ester as a white solid. ES-MS m/e (%): 339 (M+H⁺, 100).

c) (+)-(7-[1,4]Dioxan-2-yl-4-methoxy-benzothiazol-2-yl)-carbamic acid ethyl ester 9.00 g (±)-(7-[1,4]dioxan-2-yl-4-methoxy-benzothiazol-2-yl)-carbamic acid ethyl ester was subjected to separation by chiral HPLC, injecting 1.00 g compound per chromatographic run (stationary phase: Chiralpak AD; flow rate: 35 ml min⁻¹ at 17 bar, eluant: ethanol/heptane 15/85), to afford 3.30 g (+)-(7-[1,4]dioxan-2-yl-4-methoxy-benzothiazol-2-yl)-carbamic acid ethyl ester having HPLC $R_t$=150 min, $[\alpha]_D^{20}$=+24.4° (c=0.82, CHCl₃), ES-MS m/e (%): 339 (M+H⁺, 100) and 3.10 g (−)-(7-[1,4]dioxan-2-yl-4-methoxy-benzothiazol-2-yl)-carbamic acid ethyl ester having HPLC $R_t$=220 min, $[\alpha]_D^{20}$=−22.2° (c=1.00, CHCl₃), ES-MS m/e (%): 339 (M+H⁺, 100).

d) (+)-7-[1,4]Dioxan-2-yl-4-methoxy-benzothiazol-2-ylamine

To a stirred solution of 330 g (9.75 mmol) (+)-(7-[1,4]dioxan-2-yl-4-methoxy-benzothiazol-2-yl)-carbamic acid ethyl ester in 200 ml dioxane and 20 ml ethylene glycol was added 200 ml of a 2 N aq. potassium hydroxide solution and the mixture was heated at 100° C. for 2 days. After cooling to room temperature the mixture was poured onto water and extracted three times with ethyl acetate. The combined organic phases were washed with brine, then dried over sodium sulphate and concentrated in vacuo. Flash chromatography (1/9 acetone/dichloromethane) followed by trituration in ethyl acetate afforded 2.18 g (84 %) (+)-7-[1,4]dioxan-2-yl-4-methoxy-benzothiazol-2-ylamine as an off-white solid. $[\alpha]_D^{20}$=+28.2° (c=0.92, CHCl$_3$), ES-MS m/e (%): 267 (M+H$^+$, 100).

e) (+)-N-(7-[1,4]Dioxan-2-yl-4-methoxy-benzothiazol-2-yl)-2-methyl-isonicotinamide To a stirred solution of 85 mg (0.49 mmol) 2-methyl-isonicotinic acid hydrochloride in 10 ml THF were added 214 mg (0.56 mmol) HATU and 0.16 ml (0.94 mmol) N-ethyldiisopropylamine and stirring continued at room temperature for 2 h. 100 mg (0.38 mmol) (+)-7-[1,4]dioxan-2-yl-4-methoxy-benzothiazol-2-ylamine was then added and stirring continued at room temperature for 16 h. The reaction mixture was then poured into saturated aqueous sodium bicarbonate solution and extracted three times with ethyl acetate. The combined organic phases were dried over sodium sulfate and concentrated in vacuo. Flash chromatography (acetone) followed by trituration in ether afforded 100 mg (69%) (+)-N-(7-[1,4]dioxan-2-yl-4-methoxy-benzothiazol-2-yl)-2-methyl-isonicotinamide as a white solid. $[\alpha]_D^{20}$=+43.8° (c=1.04, CHCl$_3$), ES-MS m/e (%): 386 (M+H$^+$, 100).

In an analogous manner there was obtained:

Example 16

(+)-N-(7-[1,4]Dioxan-2-yl-4-methoxy-benzothiazol-2-yl)-4-fluoro-benzamide

From 4-fluoro-benzoic acid, HATU and N-ethyldiisopropylamine in THF, then treatment with (+)-7-[1,4]dioxan-2-yl-4-methoxy-benzothiazol-2-ylamine. $[\alpha]_D^{20}$=+13.3° (c=0.32, DMSO), ES-MS m/e (%): 389 (M+H$^+$, 100).

Example 17

(+)-N-(7-[1,4]Dioxan-2-yl-4-methoxy-benzothiazol-2-yl)-2-morpholin-4-yl-isonicotinamide a) (+)-2-Bromo-N-(7-[1,4]dioxan-2-yl-4-methoxy-benzothiazol-2-yl)-isonicotinamide To a stirred solution of 789 mg (3.91 mmol) 2-bromo-isonicotinic acid in 50 ml THF were added 1.71 g (4.51 mmol) HATU and 1.29 ml (7.51 mmol) N-ethyldiisopropylamine and stirring continued at room temperature for 2 h. 800 mg (3.00 mmol) (+)-7-[1,4]dioxan-2-yl-4-methoxy-benzothiazol-2-ylamine was then added and stirring continued at room temperature for 24 h. The reaction mixture was then poured into saturated aqueous sodium bicarbonate solution and extracted three times with ethyl acetate. The combined organic phases were dried over sodium sulfate and concentrated in vacuo. Flash chromatography (acetone) followed by trituration in ether afforded 1.35 g (99%) (+)-2-bromo-N-(7-[1,4]dioxan-2-yl-4-methoxy-benzothiazol-2-yl)-isonicotinamide as a light yelllow solid. $[\alpha]_D^{20}$=+12.9° (c=0.76, CHCl$_3$), ES-MS m/e (%):452 (M{$^{81}$Br}+H$^+$, 95), 450 (M{$^{79}$Br}+H$^+$, 100).

b) (+)-N-(7-[1,4]Dioxan-2-yl-4-methoxy-benzothiazol-2-yl)-2-morpholin-4-yl-isonicotinamide A stirred suspension of 100 mg (0.22 mmol) (+)-2-bromo-N-(7-[1,4]dioxan-2-yl-4-methoxy-benzothiazol-2-yl)-isonicotinamide, 145 mg (0.44 mmol) cesium carbonate and a few crystals of 2,6-di-tert-butyl-p-cresol in 0.39 ml (4.44 mmol) morpholine in a thick-walled glass pressure tube fitted with a teflon cap was heated at 100° C. for 16 h. The reaction mixture was then cooled to room temperature and concentrated in vacuo. Flash chromatography (1/1 acetone/hexane) followed by trituration in ether afforded 35 mg (35%) (+)-N-(7-[1,4]dioxan-2-yl-4-methoxy-benzothiazol-2-yl)-2-morpholin-4-yl-isonicotinamide as a white solid. $[\alpha]_D^{20}$=+63.7° (c=0.63, CHCl$_3$), ES-MS m/e (%): 457 (M+H$^+$, 100).

In an analogous manner there was obtained:

Example 18

(+)-2-Azetidin-1-yl-N-(7-[1,4]dioxan-2-yl-4-methoxy-benzothiazol-2-yl)-isonicotinamide From (+)-2-bromo-N-(7-[1,4]dioxan-2-yl-4-methoxy-benzothiazol-2-yl)-isonicotinamide with cesium carbonate and azetidine. $[\alpha]_D^{20}$=+25.5° (c=0.26, CHCl$_3$), ES-MS m/e (%): 427 (M+H$^+$, 100).

Example 19

(+)-N-(7-[1,4]Dioxan-2-yl-4-methoxy-benzothiazol-2-yl)-2-morpholin-4-ylethyl-isonicotinamide a) (+)-2-Chloromethyl-N-(7-[1,4]dioxan-2-yl-4-methoxy-benzothiazol-2-yl)-isonicotinamide To a stirred solution of 503 mg (2.93 mmol) 2-chloromethyl-isonicotinic acid in 50 ml THF were added 1.28 g (3.38 mmol) HATU and 0.96 ml (5.63 mmol) N-ethyldiisopropylamine and stirring continued at room temperature for 2 h. 600 mg (2.25 mmol) (+)-7-[1,4]dioxan-2-yl-4-methoxy-benzothiazol-2-ylamine was then added and stirring continued at room temperature for 24 h. The reaction mixture was then poured into saturated aqueous sodium bicarbonate solution and extracted three times with ethyl acetate. The combined organic phases were dried over sodium sulfate and concentrated in vacuo. Flash chromatography (acetone) followed by trituration in ether afforded 450 mg (48%) (+)-2-chloromethyl-N-(7-[1,4]dioxan-2-yl-4-methoxy-benzothiazol-2-yl)-isonicotinamide as a light yelllow solid. $[\alpha]_D^{20}$=+12.1° (c=0.41, CHCl$_3$), ES-MS m/e (%):422 (M{$^{37}$Cl}+H$^+$, 35), 420 (M{$^{35}$Cl}+H$^+$, 100).

b) (+)-N-(7-[1,4]Dioxan-2-yl-4-methoxy-benzothiazol-2-yl)-2-morpholin-4-ylmethyl-isonicotinamide A suspension of 100 mg (0.24 mmol) (+)-2-chloromethyl-N-(7-[1,4]dioxan-2-yl-4-methoxy-benzothiazol-2-yl)-isonicotinamide, 155 mg (0.48 mmol) cesium carbonate and 0.42 ml (4.76 mmol) morpholine was ultrasonicated at room temperature for 10 min. The reaction mixture was then concentrated in vacuo. Flash chromatography (1/1 acetone/hexane) followed by trituration in ether and hexane afforded 70 mg (62%) (+)-N-(7-[1,4]dioxan-2-yl-4-methoxy-benzothiazol-2-yl)-2-morpholin-4-ylmethyl-isonicotinamide as an off-white solid. $[\alpha]_D^{20}$=+89.2° (c=0.49, CHCl$_3$), ES-MS m/e (%): 471 (M+H$^+$, 100).

In an analogous manner there were obtained:

Example 20

(+)-N-(7-[1,4]Dioxan-2-yl-4-methoxy-benthiazol-2-yl)-2-pyrrolidin-1-ylmethyl-isonicotinamide From (+)-2-chloromethyl-N-(7-[1,4]dioxan-2-yl-4-methoxy-benzothiazol-2-yl)-isonicotinamide with cesium carbonate and pyrrolidine. $[\alpha]_D^{20}$=+43.0° (c=0.71, CHCl$_3$), ES-MS m/e (%): 455 (M+H$^+$, 100).

Example 21

(+)-2-Diethylaminomethyl-N-(7-[1,4]dioxan-2-yl-4-methoxy-benzothiazol-2-yl)-isonicotinamide From (+)-2-chloromethyl-N-(7-[1,4]dioxan-2-yl-4-methoxy-benzothiazol-2-yl)-isonicotinamide with cesium carbonate and diethylamine. $[\alpha]_D^{20}$=+48.9° (c=1.02, CHCl$_3$), ES-MS m/e (%): 457 (M+H$^+$, 100).

Example 22

(+)-N-(7-[1,4]Dioxan-2-yl-4-methoxy-benzothiazol-2-yl)-2-{[(2-methoxy-ethyl)-methyl-amino]-methyl}-isonicotinamide From (+)-2-chloromethyl-N-(7-[1,4]dioxan-2-yl-4-methoxy-benzothiazol-2-yl)-isonicotinamide with cesium carbonate and N-(2-methoxyethyl)methylamine. $[\alpha]_D^{20}$=+58.7° (c=1.01, CHCl$_3$), ES-MS m/e (%): 473 (M+H$^+$, 100).

Example 23

(+)-cis-3-(7-[1,4]Dioxan-2-yl-4-methoxy-benzothiazol-2-yl)-1-(4-hydroxy-cyclohexyl)-1-methyl-urea a) (+)-(7-[1,4]Dioxan-2-yl-4-methoxy-benzothiazol-2-yl)-carbamic acid phenyl ester To a stirred suspension of 450 mg (1.69 mmol) (+)-7-[1,4]dioxan-2-yl-4-methoxy-benzothiazol-2-ylamine and 0.41 ml (5.07 mmol) pyridine in 10 ml dichloromethane at 0° C. was added 0.28 ml (2.20 mmol) phenyl chloroformate and stirring continued at room temperature for 16 h. The reaction mixture was then poured into saturated aqueous sodium bicarbonate solution and extracted three times with ethyl acetate. The combined organic phases were dried over sodium sulfate and concentrated in vacuo. Flash chromatography (1/1 acetone/heptane) followed by trituration in ether and hexane afforded 630 mg (96%) (+)-(7-[1,4]dioxan-2-yl-4-methoxy-benzothiazol-2-yl)-carbamic acid phenyl ester as a white solid. $[\alpha]_D^{20}$=+13.6° (c=0.32, CHCl$_3$), ES-MS m/e (%):387 (M+H$^+$, 100).

b) (+)-Cis-3-(7-[1,4]Dioxan-2-yl-4-methoxy-benzothiazol-2-yl)-1-(4-hydroxy-cyclohexyl)-1-methyl-urea To a stirred solution of 100 mg (0.26 mmol) (+)-(7-[1,4]dioxan-2-yl-4-methoxy-benzothiazol-2-yl)-carbamic acid phenyl ester and 0.06 ml (0.78 mmol) pyridine in 5 ml chloroform at room temperature was added 47 mg (0.36 mmol) cis-4-methylamino-cyclohexanol and stirring continued at 50° C. for 16 h. The reaction mixture was then concentrated in vacuo. Flash chromatography (1/1 acetone/heptane then acetone) followed by trituration in ether and hexane afforded 75 mg (69%) (+)-cis-3-(7-[1,4]dioxan-2-yl-4-methoxy-benzothiazol-2-yl)-1-(4-hydroxy-cyclohexyl)-1-methyl-urea as a white solid. $[\alpha]_D^{20}$=+18.8° (c=1.07, CHCl$_3$), ES-MS m/e (%): 422 (M+H$^+$, 100).

In an analogous manner there were obtained:

Example 24

(+)-trans-3-(7-[1,4]Dioxan-2-yl-4-methoxy-benzothiazol-2-yl)-1-(4-hydroxy-cyclohexyl)-1-methyl-urea From (+)-(7-[1,4]dioxan-2-yl-4-methoxy-benzothiazol-2-yl)-carbamic acid phenyl ester with trans-4-methylamino-cyclohexanol and pyridine in chloroform. $[\alpha]_D^{20}$=+20.5° (c=1.02, CHCl$_3$), ES-MS m/e (%): 422 (M+H$^+$, 100).

Example 25

(+)-4-Hydroxy-piperidine-1-carboxylic acid (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with 4-hydroxypiperidine and pyridine in chloroform. $[\alpha]_D^{20}$=+29.4° (c=1.01, CHCl$_3$), ES-MS m/e (%): 394 (M+H$^+$, 100).

Example 26

(+)-Morpholine-4-carboxylic acid (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with morpholine and pyridine in chloroform. $[\alpha]_D^{20}$=+43.1° (c=1.05, CHCl$_3$), ES-MS m/e (%): 380 (M+H$^+$, 100).

Example 27

(+)-N-(7-[1,4]Dioxan-2-yl-4-methoxy-benzothiazol-2-yl)-2-ethoxymethyl-isonicotinamide To a solution of 50 mg (0.12 mmol) (+)-2-chloromethyl-N-(7-[1,4]dioxan-2-yl-4-methoxy-benzothiazol-2-yl)-isonicotinamide in 2 ml ethanol was added 1.32 ml (3.57 mmol) sodium ethylate solution (2.71 M solution in ethanol) and the mixture ultrasonicated at room temperature for 2 h. The reaction mixture was then poured onto water and extracted three times with dichloromethane. The organic phases were dried over sodium sulfate and concentrated in vacuo. Flash chromatography (1/1 acetone/heptane) followed by trituration in ether afforded 35 mg (68%) (+)-N-(7-[1,4]dioxan-2-yl-4-methoxy-benzothiazol-2-yl)-2-ethoxymethyl-isonicotinamide as an off-white solid. $[\alpha]_D^{20}$=+60.7° (c=0.94, CHCl$_3$), ES-MS m/e (%): 430 (M+H$^+$, 100).

In an analogous manner there was obtained:

Example 28

(+)-N-(7-[1,4]Dioxan-2-yl-4-methoxy-benzothiazol-2-yl)-2-methoxymethyl-isonicotinamide From (+)-2-chloromethyl-N-(7-[1,4]dioxan-2-yl-4-methoxy-benzothiazol-2-yl)-isonicotinamide with sodium methylate in methanol. $[\alpha]_D^{20}$=+65.1° (c=0.55, CHCl$_3$), ES-MS m/e (%): 416 (M+H$^+$, 100).

Analogously to Example 17 there were obtained

Example 29

(+)-4-Hydroxy-3,4,5,6-tetrahydro-2H-[1,2']bipyridinyl-4'-carboxylic acid (7-[1,4]dioxan-2-yl-4-methoxy-benzothiazol-2-yl)-amide From (+)-2-bromo-N-(7-[1,4]dioxan-2-yl-4-methoxy-benzothiazol-2-yl)-isonicotinamide with cesium carbonate and 4-hydroxypiperidine in DMF. $[\alpha]_D^{20}$=+16.1° (c=0.35, DMSO), ES-MS m/e (%): 471 (M+H$^+$, 100).

Example 30

(+)-N-(7-[1,4]Dioxan-2-yl-4-methoxy-benzothiazol-2-yl)-2-(3-fluoro-azetidin-1-yl)-isonicotinamide From (+)-2-bromo-N-(7-[1,4]dioxan-2-yl-4-methoxy-benzothiazol-2-yl)-isonicotinamide with cesium carbonate and 3-fluoro-azetidine hydrochloride in DMF. $[\alpha]_D^{20}$=+19.7° (c=0.17, CHCl$_3$), ES-MS m/e (%): 445 (M+H$^+$, 100).

Example 31
(+)-N-(7-[1,4]Dioxan-2-yl-4-methoxy-benzothiazol-2-yl)-2-(3-ethoxy-azetidin-1-yl)-isonicotinamide From (+)-2-bromo-N-(7-[1,4]dioxan-2-yl-4-methoxy-benzothiazol-2-yl)-isonicotinamide with cesium carbonate and 3-ethoxy-azetidine hydrochloride in DMF. $[\alpha]_D^{20}=+44.3°$ (c=0.57, CHCl$_3$), ES-MS m/e (%): 471 (M+H$^+$, 100).

Example 32
(+)-N-(7-[1,4]Dioxan-2-yl-4-methoxy-benzothiazol-2-yl)-2-(3-methoxy-azetidin-1-yl)-isonicotinamide From (+)-2-bromo-N-(7-[1,4]dioxan-2-yl-4-methoxy-benzothiazol-2-yl)-isonicotinamide with cesium carbonate and 3-methoxy-azetidine hydrochloride in DMF. $[\alpha]_D^{20}=+42.5°$ (c=0.44, CHCl$_3$), ES-MS m/e (%): 457 (M+H$^+$, 100).

Analogously to Example 15 there were obtained

Example 33
(+)-N-(7-[1,4]Dioxan-2-yl-4-methoxy-benzothiazol-2-yl)-4-methoxy-benzamide From para-anisic acid, HATU and N-ethyldiisopropylamine in THF, then treatment with (+)-7-[1,4]dioxan-2-yl-4-methoxy-benzothiazol-2-ylamine. $[\alpha]_D^{20}=+28.2°$ (c=0.33 CHCl$_3$), ES-MS m/e (%): 401 (M+H$^+$, 100).

Example 34
(+)-N-(7-[1,4]Dioxan-2-yl-4-methoxy-benzothiazol-2-yl)-4-methyl-benzamide From para-toluic acid, HATU and N-ethyldiisopropylamine in THF, then treatment with (+)-7-[1,4]dioxan-2-yl-4-methoxy-benzothiazol-2-ylamine. $[\alpha]_D^{20}=+35.1°$ (c=0.84, CHCl$_3$), ES-MS m/e (%): 385 (M+H$^+$, 100).

Example 35
(+)-N-(7-[1,4]Dioxan-2-yl-4-methoxy-benzothiazol-2-yl)-2,4-dimethyl-benzamide From 2,4-dimethylbenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+7.4°$ (c=0.77, CHCl$_3$), ES-MS m/e (%): 399 (M+H$^+$, 100).

Example 36
(+)-Benzo[1,3]dioxole-5-carboxylic acid (7-[1,4]dioxan-2-yl-4-methoxy-benzothiazol-2-yl)-amide From piperonylic acid, HATU and N-ethyldiisopropylamine in THF, then treatment with (+)-7-[1,4]dioxan-2-yl-4-methoxy-benzothiazol-2-ylamine. $[]_D^{20}=+25.7°$ (c=0.86, CHCl$_3$), ES-MS m/e (%): 415 (M+H$^+$, 100).

Example 37
(+)-N-(7-[1,4]Dioxan-2-yl-4-methoxy-benzothiazol-2-yl)-3-methoxy-benzamide From 3-methoxybenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+24.3°$ (c=0.79, CHCl$_3$), ES-MS m/e (%): 401 (M+H$^+$, 100).

Example 38
(+)-N-(7-[1,4]Dioxan-2-yl-4-methoxy-benzothiazol-2-yl)-3-methyl-benzamide From meta-toluic acid, HATU and N-ethyldiisopropylamine in THF, then treatment with (+)-7-[1,4]dioxan-2-yl-4-methoxy-benzothiazol-2-ylamine. $[\alpha]_D^{20}=+17.7°$ (c=0.79, CHCl$_3$), ES-MS m/e (%): 385 (M+H$^+$, 100).

Example 39
(+)-N-(7-[1,4]Dioxan-2-yl-4-methoxy-benzothiazol-2-yl)-3-fluoro-benzamide From 3-fluorobenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+31.0°$ (c=0.70, CHCl$_3$), ES-MS m/e (%): 389 (M+H$^+$, 100).

Example 40
(+)-N-(7-[1,4]Dioxan-2-yl-4-methoxy-benzothiazol-2-yl)-3,4-dimethoxy-benzamide From 3,4-dimethoxybenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+33.4°$ (c=0.53, CHCl$_3$), ES-MS m/e (%): 431 (M+H$^+$, 100).

Example 41
(+)-3-Dimethylamino-N-(7-[1,4]dioxan-2-yl-4-methoxy-benzothiazol-2-yl)-benzamide From 3-dimethylaminobenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+18.7°$ (c=1.06, CHCl$_3$), ES-MS m/e (%): 414 (M+H$^+$, 100).

Example 42
(+)-N-(7-[1,4]Dioxan-2-yl-4-methoxy-benzothiazol-2-yl)-3-methoxy-4-methyl-benzamide From 3-methoxy-4-methylbenzoic acid, HATU and N-ethyldiisopropylamine in THP, then treatment with (+)-7-[1,4]dioxan-2-yl-4-methoxy-benzothiazol-2-ylamine. $[\alpha]_D^{20}=+23.0°$ (c=1.03, CHCl$_3$), ES-MS m/e (%): 415 (M+H$^+$, 100).

Example 43
(+)-N-(7-[1,4]Dioxan-2-yl-4-methoxy-benzothiazol-2-yl)-2-fluoro-benzamide From 2-fluorobenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+20.0°$ (c=1.00, CHCl$_3$), ES-MS m/e (%): 389 (M+H$^+$, 100).

Example 44
(+)-N-(7-[1,4]Dioxan-2-yl-4-methoxy-benzothiazol-2-yl)-2,4-difluoro-benzamide From 2,4-difluorobenzoic acid, HATU and N-ethyldiisopropylamine in THF, then treatment with (+)-7-[1,4]dioxan-2-yl-4-methoxy-benzothiazol-2-ylamine. $[\alpha]_D^{20}=+19.4°$ (c=1.00, CHCl$_3$), ES-MS m/e (%): 407 (M+H$^+$, 100).

Example 45
(+)-N-(7-[1,4]Dioxan-2-yl-4-methoxy-benzothiazol-2-yl)-2-fluoro-4-methoxy-benzamide From 2-fluoro-4-methoxybenzoic acid, HATU and N-ethyldiisopropylamine in THF, then treatment with (+)-7-[1,4]dioxan-2-yl-4-methoxy-benzothiazol-2-ylamine. $[\alpha]_D^{20}$=+19.4° (c=1.02, CHCl$_3$), ES-MS m/e (%): 419 (M+H$^+$, 100).

Example 46
(+)-4-Dimethylamino-N-(7-[1,4]dioxan-2-yl-4-methoxy-benzothiazol-2-yl)-benzamide From 4-dimethylaminobenzoic acid, HATU and N-ethyldiisopropylamine in THF, then treatment with (+)-7-[1,4]dioxan-2-yl-4-methoxy-benzothiazol-2-ylamine. $[\alpha]_D^{20}$=+22.6° (c=0.45, CHCl$_3$), ES-MS m/e (%): 414 (M+H$^+$, 100).

Example 47
(+)-N-(7-[1,4]Dioxan-2-yl-4-methoxy-benzothiazol-2-yl)-2-ethoxy-isonicotinamide From 2-ethoxy-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+31.7° (c=0.61, CHCl$_3$), ES-MS m/e (%): 416 (M+H$^+$, 100).

Example 48
(+)-N-(7-[1,4]Dioxan-2-yl-4-methoxy-benzothiazol-2-yl)-4-methoxy-2-methyl-benzamide From 4-methoxy-2-methylbenzoic acid, HATU and N-ethyldiisopropylamine in THF, then treatment with (+)-7-[1,4]dioxan-2-yl-4-methoxy-benzothiazol-2-ylamine. $[\alpha]_D^{20}$=+19.7° (c=0.62, CHCl$_3$), ES-MS m/e (%): 415 (M+H$^+$, 100).

Analogously to Example 17 there was obtained

Example 49
(+)-N-(7-[1,4]Dioxan-2-yl-4-methoxy-benzothiazol-2-yl)-2-(3-hydroxy-azetidin-1-yl)-isonicotinamide From (+)-2-bromo-N-(7-[1,4]dioxan-2-yl-4-methoxy-benzothiazol-2-yl)-isonicotinamide with cesium carbonate and azetidin-3-ol hydrochloride in NMP. $[\alpha]_D^{20}$=+12.2° (c=0.51, DMSO), ES-MS m/e (%): 443 (M+H$^+$, 100).

Analogously to Example 15 there were obtained

Example 50
(+)-N-(7-[1,4]Dioxan-2-yl-4-methoxy-benzothiazol-2-yl)-2,3-dimethyl-benzamide From 2,3-dimethylbenzoic acid, HATU and N-ethyldiisopropylamine in THF, then treatment with (+)-7-[1,4]dioxan-2-yl-4-methoxy-benzothiazol-2-ylamine. $[\alpha]_D^{20}$=+16.4° (c=0.46, CHCl$_3$), ES-MS m/e (%): 399 (M+H$^+$, 100).

Example 51
(+)-N-(7-[1,4]Dioxan-2-yl-4-methoxy-benzothiazol-2-yl)-2,4-dimethoxy-benzamide From 2,4-dimethoxybenzoic acid, HATU and N-ethyldiisopropylamine in THF, then treatment with (+)-7-[1,4]dioxan-2-yl-4-methoxy-benzothiazol-2-ylamine. $[\alpha]_D^{20}$=+21.7° (c=0.50, CHCl$_3$), ES-MS m/e (%): 431 (M+H$^+$, 100).

Example 52
(+)-N-(7-[1,4]Dioxan-2-yl-4-methoxy-benzothiazol-2-y)-2-(2-morpholin-4-yl-ethoxy)-isonicotinamide To a solution of 437 mg (3.33 mmol) N-(2-hydroxyethyl)morpholine and 20 mg (0.09 mmol) 2,6-di-tert-butyl-para-cresol in 5 ml dioxane and 1 ml DMF was added portionwise 194 mg (4.44 mmol) sodium hydride (55% dispersion in oil) and the mixture heated at 50° C. for 30 min. 200 mg (0.44 mmol) (+)-2-bromo-N-(7-[1,4]dioxan-2-yl-4-methoxy-benzothiazol-2-yl)-isonicotinamide was then added and the mixture heated at 80° C. for 16 h. The reaction mixture was then poured onto water and extracted three times with ethyl acetate. The organic phases were dried over sodium sulfate and concentrated in vacuo. Flash chromatography (5/95 methanol/ethyl acetate) followed by trituration in ether and hexane afforded 160 mg (72%) (+)-N-(7-[1,4]dioxan-2-yl-4-methoxy-benzothiazol-2-yl)-2-(2-morpholin-4-yl-ethoxy)-isonicotinamide as a white solid. $[\alpha]_D^{20}$=+51.2° (c=1.04, CHCl$_3$), ES-MS m/e (%): 501 (M+H$^+$, 100).

Analogously to Example 15 there were obtained

Example 53
(+)-N-(7-[1,4]Dioxan-2-yl-4-methoxy-benzothiazol-2-yl)-5-methoxy-nicotinamide From 5-methoxy-nicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+5.8° (c=0.10, DMSO), ES-MS m/e (%): 402 (M+H$^+$, 100).

Example 54
(+)-N-(7-[1,4]Dioxan-2-yl-4-methoxy-benzothiazol-2-y)-2-phenyl-acetamide From phenylacetic acid, HATU and N-ethyldiisopropylamine in THF, then treatment with (+)-7-[1,4]dioxan-2-yl-4-methoxy-benzothiazol-2-ylamine. $[\alpha]_D^{20}$=+22.7° (c=1.04, CHCl$_3$), ES-MS m/e (%): 385 (M+H$^+$, 100).

Example 55
(+)-N-(7-[1,4]Dioxan-2-yl-4-methoxy-benzothiazol-2-yl)-2-methoxy-acetamide From methoxyacetic acid, HATU and N-ethyldiisopropylamine in THF, then treatment with (+)-7-[1,4]dioxan-2-yl-4-methoxy-benzothiazol-2-ylamine. $[\alpha]_D^{20}$=+24.9° (c=1.05, CHCl$_3$), ES-MS m/e (%): 339 (M+H$^+$, 100).

Example 56
(+)-N-(7-[1,4]Dioxan-2-yl-4-methoxy-benzothiazol-2-yl)-3-methoxy-propionamide From 3-methoxypropionic acid, HATU and N-ethyldiisopropylamine in THF, then treatment with (+)-7-[1,4]dioxan-2-yl-4-methoxy-benzothiazol-2-ylamine. $[\alpha]_D^{20}$=+24.4° (c=1.02, CHCl$_3$), ES-MS m/e (%): 353 (M+H$^+$, 100).

Example 57
(+)-2-Cyclohexyl-N-(7-[1,4]dioxan-2-yl-4-methoxy-benzothiazol-2-yl)-acetamide From cyclohexylacetic add, HATU and N-ethyldiisopropylamine in THF, then treatment with (+)-7-[1,4]dioxan-2-yl-4-methoxy-benzothiazol-2-ylamine. $[\alpha]_D^{20}$=+19.3° (c=1.02, CHCl$_3$), ES-MS m/e (%): 391 (M+H$^+$, 100).

Analogously to Example 52 there were obtained

Example 58

(+)-N-(7-[1,4]Dioxan-2-yl-4-methoxy-benzothiazol-2-yl)-2-(2,2,2-trifluoro-ethoxy)-isonicotinamide From (+)-2-bromo-N-(7-[1,4]dioxan-2-yl-4-methoxy-benzothiazol-2-yl)-isonicotinamide sodium hydride and 2,2,2-trifluoroethanol in dioxane and DMF. $[\alpha]_D^{20}$=+11.3° (c=0.11, CHCl$_3$), ES-MS m/e (%): 470 (M+H$^+$, 100).

Example 59

(+)-2-Cyclopropylmethoxy-N-(7-[1,4]dioxan-2-yl-4-methoxy-benzothiazol-2-yl)-isonicotinamide From (+)-2-bromo-N-(7-[1,4]dioxan-2-yl-4-methoxy-benzothiazol-2-yl)-isonicotinamide sodium hydride and hydroxymethylcyclopropane in dioxane and DMF. $[\alpha]_D^{20}$=+39.2° (c=1.02, CHCl$_3$), ES-MS m/e (%): 442 (M+H$^+$, 100).

Example 60

(+)-N-(7-[1,4]Dioxan-2-yl-4-methoxy-benzothiazol-2-yl)-2-(tetrahydro-pyran-4-yloxy)-isonicotinamide From (+)-2-bromo-N-(7-[1,4]dioxan-2-yl-4-methoxy-benzothiazol-2-yl)-isonicotinamide sodium hydride and tetrahydro-2H-pyranol-4-ol in dioxane and DMF. $[\alpha]_D^{20}$=+12.4° (c=0.11, CHCl$_3$), ES-MS m/e (%): 472 (M+H$^+$, 100).

Example 61

(+)-N-(7-[1,4]Dioxan-2-yl-4-methoxy-benzothiazol-2-yl)-2-(2-methoxy-ethoxy)-isonicotinamide From (+)-2-bromo-N-(7-[1,4]dioxan-2-yl-4-methoxy-benzothiazol-2-yl)-isonicotinamide sodium hydride and 2-methoxyethanol in dioxane and DMF. $[\alpha]_D^{20}$=+17.6° (c=0.15, CHCl$_3$), ES-MS m/e (%): 446 (M+H$^+$, 100).

Analogously to Example 15 there were obtained

Example 62

(+)-N-(7-[1,4]Dioxan-2-yl-4-methoxy-benzothiazol-2-yl)-2-(tetrahydro-pyran-4-yl)-acetamide From tetrahydropyran-4-yl-acetic acid, HATU and N-ethyldiisopropylamine in THF, then treatment with (+)-7-[1,4]dioxan-2-yl-4-methoxy-benzothiazol-2-ylamine. $[\alpha]_D^{20}$=+24.1° (c=1.07, CHCl$_3$), ES-MS m/e (%): 393 (M+H$^+$, 100).

Example 63

(+)-N-(7-[1,4]Dioxan-2-yl-4-methoxy-benzothiazol-2-yl)-2-pyridin-2-yl-acetamide

From 2-pyridylacetic acid hydrochloride, HATU and N-ethyldiisopropylamine in THF, then treatment with (+)-7-[1,4]dioxan-2-yl-4-methoxy-benzothiazol-2-ylamine. $[\alpha]_D^{20}$=+26.8° (c=0.51, CHCl$_3$), ES-MS m/e (%): 386 (M+H$^+$, 100).

Example 64

(+)-Cyclohexanecarboxylic acid (7-[1,4]dioxan-2-yl-4-methoxy-benzothiazol-2-yl)-amide From cyclohexanecarboxylic acid, HATU and N-ethyldiisopropylamine in THF, then treatment with (+)-7-[1,4]dioxan-2-yl-4-methoxy-benzothiazol-2-ylamine. $[\alpha]_D^{20}$=+19.2° (c=1.05, CHCl$_3$), ES-MS m/e (%): 377 (M+H$^+$, 100).

Example 65

(+)-N-(7-[1,4]Dioxan-2-yl-4-methoxy-benzothiazol-2-yl)-2-(2-methoxy-ethoxymethyl)-isonicotinamide From 2-(2-methoxy-ethoxymethyl)-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+69.2° (c=1.04, CHCl$_3$), ES-MS m/e (%): 460 (M+H$^+$, 100).

Example 66

(+)-2-Cyclopropylmethoxymethyl-N-(7-[1,4]dioxan-2-yl-4-methoxy-benzothiazol-2-yl)-isonicotinamide From 2-cyclopropylmethoxymethyl-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+6.7° (c=1.04, CHCl$_3$), ES-MS m/e (%): 456 (M+H$^+$, 100).

Example 67

(+)-N-(7-[1,4]Dioxan-2-yl-4-methoxy-benzothiazol-2-yl)-2-(2,2,2-trifluoro-ethoxymethyl)-isonicotinamide From 2-(2,2,2-trifluoro-ethoxymethyl)-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+121.3° (c=1.05, CHCl$_3$), ES-MS m/e (%): 484 (M+H$^+$, 100).

Example 68

(+)-N-(7-[1,4]Dioxan-2-yl-4-methoxy-benzothiazol-2-yl)-2-(tetrahydro-pyran-4-yloxymethyl)-isonicotinamide From 2-(tetrahydro-pyran-4-yloxymethyl)-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+84.9° (c=1.05, CHCl$_3$), ES-MS m/e (%): 486 (M+H$^+$, 100).

Example 69

(+)-6-Methoxy-pyridine-2-carboxylic acid (7-[1,4]dioxan-2-yl-4-methoxy-benzothiazol-2-yl)-amide From 6-methoxy-2-pyridinecarboxylic acid, HATU and N-ethyldiisopropylamine in THF, then treatment with (+)-7-[1,4]dioxan-2-yl-4-methoxy-benzothiazol-2-ylamine. $[\alpha]_D^{20}$=+20.3° (c=1.08, CHCl$_3$), ES-MS m/e (%): 402 (M+H$^+$, 100).

Example 70

(+)-N-(7-[1,4]Dioxan-2-yl-4-methoxy-benzothiazol-2-yl)-2-[2-(2-oxo-pyrrolidin-1-yl)-ethoxy]-isonicotinamide From 2-[2-(2-oxo-pyrrolidin-1-yl)-ethoxy]-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+57.3° (c=1.03, CHCl$_3$), ES-MS m/e (%): 499 (M+H$^+$, 100).

Example 71

(+)-N-(7-[1,4]Dioxan-2-yl-4-methoxy-benzothiazol-2-yl)-2-[2-(2-oxo-pyrrolidin-1-yl)-ethoxymethyl]-isonicotinamide From 2-[2-(2-oxo-pyrrolidin-1-yl)-ethoxymethyl]-isonicotinic acid, HATU and N-ethyldiisopropylamine in THF, then treatment with (+)-7-[1,4]dioxan-2-yl-4-methoxy-benzothiazol-2-ylamine. $[\alpha]_D^{20}$=+84.1° (c=1.02, CHCl$_3$), ES-MS m/e (%): 513 (M+H$^+$, 100).

Example 72
(+)-N-(7-[1,4]Dioxan-2-yl-4-methoxy-benzothiazol-2-yl)-N',N'-dimethyl-succinamide From N,N-dimethylsuccinamic acid, HATU and N-ethyldiisopropylamine in THF, then treatment with (+)-7-[1,4]dioxan-2-yl-4-methoxy-benzothiazol-2-ylamine. $[\alpha]_D^{20}$=+21.9° (c=1.04, CHCl$_3$), ES-MS m/e (%): 394 (M+H$^+$, 100).

Example 73
(+)-N-(7-[1,4]Dioxan-2-yl-4-methoxy-benzothiazol-2-yl)-3-(2-oxo-pyrrolidin-1-yl)-propionamide From 2-oxo-1-pyrrolidinepropionic acid, HATU and N-ethyldiisopropylamine in THF, then treatment with (+)-7-[1,4]dioxan-2-yl-4-methoxy-benzothiazol-2-ylamine. $[\alpha]_D^{20}$=+21.5° (c=1.05, CHCl$_3$), ES-MS m/e (%): 406 (M+H$^+$, 100).

Example 74
(+)-N-(7-[1,4]Dioxan-2-yl-4-methoxy-benzothiazol-2-yl)-2-(6-methyl-pyridin-3-yl)-acetamide From (6-methyl-pyridin-3-yl)-acetic acid, HATU and N-ethyldiisopropylamine in THF, then treatment with (+)-7-[1,4]dioxan-2-yl-4-methoxy-benzothiazol-2-ylamine. $[\alpha]_D^{20}$=+22.8° (c=1.06, CHCl$_3$), ES-MS m/e (%): 400 (M+H$^+$, 100).

Example 75
(+)-4-Dimethylamino-N-(7-[1,4]dioxan-2-yl-4-methoxy-benzothiazol-2-yl)-butyramide From 4-(dimethylamino)butyric acid hydrochloride, HATU and N-ethyldiisopropylamine in THF, then treatment with (+)-7-[1,4]dioxan-2-yl-4-methoxy-benzothiazol-2-ylamine. $[\alpha]_D^{20}$=+24.2° (c=0.53, CHCl$_3$), ES-MS m/e (%): 380 (M+H$^+$, 100).

Analogously to Example 23 there were obtained

Example 76
(−)-(1S,4S)-2-Oxa-5-aza-bicyclo[2.2.1]heptane-5-carboxylic acid (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with (1S,4S)-2-oxa-5-aza-bicyclo[2.2.1]heptane trifluoroacetate and pyridine in chloroform. $[\alpha]_D^{20}$=−11.9° (c=0.51, CHCl$_3$), ES-MS m/e (%): 392 (M+H$^+$, 100).

Example 77
(+)-4-Hydroxy-4-methyl-piperidine-1-carboxylic acid (7-[1,4]dioxan-2-yl-4-methoxy-benzothiazol-2-yl)-amide From (+)-(7-[1,4]dioxan-2yl-4-methoxy-benzothiazol-2-yl)-carbamic acid phenyl ester with 4-methyl-piperidin-4-ol and pyridine in chloroform. $[\alpha]_D^{20}$=+25.2° (c=1.07, CHCl$_3$), ES-MS m/e (%): 408 (M+H$^+$, 100).

Example 78
(+)-4-Hydroxymethyl-piperidine-1-carboxylic add (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with piperidin-4-yl-methanol and pyridine in chloroform. $[\alpha]_D^{20}$=+22.4° (c=1.04, CHCl$_3$), ES-MS m/e (%): 408 (M+H$^+$, 100).

Analogously to Example 15 there was obtained

Example 79
(+)-N-(7-[1,4]Dioxan-2-y-4-methoxy-benzothiazol-2-yl)-2-morpholin-4-yl-acetamide From morpholin-4-yl-acetic acid, HATU and N-ethyldiisopropylamine in THF, then treatment with (+)-7-[1,4]dioxan-2-yl-4-methoxy-benzothiazol-2-ylamine. $[\alpha]_D^{20}$=+18.8° (c=1.04, CHCl$_3$), ES-MS m/e (%): 394 (M+H$^+$, 100).

Analogously to Example 23 there were obtained

Example 80
(+)-cis-3-(7-[1,4]Dioxan-2-yl-4-methoxy-benzothiazol-2-yl)-1-(4-hydroxy-4-methyl-cyclohexyl)-1-methyl-urea From (+)-(7-[1,4]dioxan-2-yl-4-methoxy-benzothiazol-2-yl)-carbamic acid phenyl ester with cis-1-methyl-4-methylamino-cyclohexanol and N-ethyldiisopropylamine in chloroform. $[\alpha]_D^{20}$=+19.2° (c=1.05, CHCl$_3$), ES-MS m/e (%): 436 (M+H$^+$, 100).

Example 81
(+)-1-Oxa-8-aza-spiro[4.5]decane-8-carboxylic acid (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with 1-oxa-8-aza-spiro[4.5]decane trifluoroacetate and N-ethyldiisopropylamine in chloroform. $[\alpha]_D^{20}$=+25.8° (c=1.01, CHCl$_3$), ES-MS m/e (%): 434 (M+H$^+$, 100).

Example 82
(+)-4-Methoxymethyl-piperidine-1-carboxylic acid (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with 4-methoxymethyl-piperidine trifluoroacetate and N-ethyldiisopropylamine in chloroform. $[\alpha]_D^{20}$=+23.0° (c=1.04, CHCl$_3$), ES-MS m/e (%): 422 (M+H$^+$, 100).

Example 83
(+)-4-Hydroxymethyl-4-methyl-piperidine-1-carboxylic acid (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with (4-methyl-piperidin-4-yl)-methanol trifluoroacetate and N-ethyldiisopropylamine in chloroform $[\alpha]_D^{20}$=+24.1° (c=1.02, CHCl$_3$), ES-MS m/e (%): 422 (M+H$^+$, 100).

Example 84
(+)-4-Methoxymethyl-4-methyl-piperidine-1-carboxylic add (7-[1,4]dioxan-2-yl-4-methoxy-benzothiazol-2-yl)-amide From (+)-(7-[1,4]dioxan-2-yl-4-methoxy-benzothiazol-2-yl)-carbamic acid phenyl ester with 4-methoxymethyl-4-methyl-piperidine trifluoroacetate and N-ethyldiisopropylamine in chloroform. $[\alpha]_D^{20}$=+21.9° (c=0.70, CHCl$_3$), ES-MS m/e (%): 436 (M+H$^+$, 100).

What is claimed is:

1. A compound of formula I

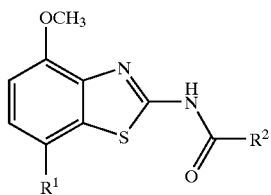

wherein $R^1$ is selected from (RS)-[1,4]dioxan-2-yl-, (R)-[1,4]dioxan-2-yl-, and (S)-[1,4]dioxan-2-yl-;

$R^2$ is a)
- —$(CH_2)_n$-pyridin-2,3 or 4-yl, or
- —$(CH_2)_n$-pyridin-2,3 or 4-yl substituted by
  - -lower alkyl,
  - —$(CH_2)_m$—O-lower alkyl,
  - —$(CH_2)_m$NR'R",
  - —$(CH_2)_m$morpholinyl,
  - —$(CH_2)_m$-pyrrolidin-1-yl,
  - —$(CH_2)_m$-piperidine-1-yl,
  - —$(CH_2)_m$-piperidine-1-yl substituted by hydroxy,
  - —$(CH_2)_m$—O—$(CH_2)_o$—$CF_3$,
  - —$(CH_2)_n$—O—$(CH_2)_m$-cycloalkyl,
  - —$(CH_2)_m$—O—$(CH_2)_o$—O-lower alkyl,
  - —$(CH_2)_m$—O—$(CH_2)_o$-2-oxo-pyrrolidin-1-yl,
  - —$(CH_2)_m$—O-tetrahydropyran-4-yl
  - —$(CH_2)_m$—O—$(CH_2)_o$-morpholinyl,
  - -di-hydropyran-4-yl,
  - -tetra-hydropyran-4-yl
  - -azetidin-1-yl, or
  - -azetidin-1-yl substituted by halogen, lower alkoxy or hydroxy; or b)
- —$(CH_2)_n$-piperidine-1-yl, or
- —$(CH_2)_n$-piperidine-1-yl substituted by one or two substituents selected from
  - -hydroxy, -hydroxy-lower alkyl, -lower alkyl and —$(CH_2)_m$—O-lower alkyl; or c)
- —$(CH_2)_n$-phenyl, or
- —$(CH_2)_n$-phenyl substituted by one or two substituents selected from
  - -halogen, -lower alkyl, -lower alkoxy and —$(CH_2)_n$—NR'R"; or d)
- -benzo[1.3]dioxol-5-yl;
- —$(CH_2)_n$-morpholinyl;
- —$(CH_2)_n$-tetrahydropyran-4-yl;
- —$(CH_2)_n$—O-lower alkyl;
- —$(CH_2)_n$-cycloalkyl;
- —$(CH_2)_n$—C(O)—NR'R";
- —$(CH_2)_n$-2-oxo-pyrrolidin-1-yl;
- —$(CH_2)_n$NR'R";
- -2-oxa-5-aza-bicyclo[2.2.1]heptane-5-yl; or
- -1-oxa-8-aza-spiro[4.5]decane-8-yl;

R' and R" are each independently selected from lower alkyl; —$(CH_2)_o$—O-lower alkyl; cycloalkyl; lower alkyl substituted by one or more substituents selected from hydroxy and lower alkyl; —$(CH_2)_o$—O-lower alkyl substituted by one or more substituents selected from hydroxy and lower alkyl; and cycloalkyl substituted by one or more substituents selected from hydroxy and lower alkyl;

n is 0, 1, 2 or 3;

m is 0 or 1; and o is 1 or 2;

or a pharmaceutically acceptable salt thereof.

2. A compound of formula I

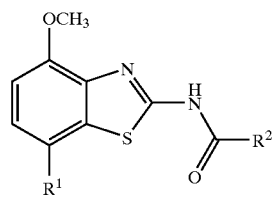

wherein $R^1$ is selected from (RS)-[1,4]dioxan-2-yl-, (R)-[1,4]dioxan-2-yl-, and (S)-[1,4]dioxan-2-yl-;

$R^2$ is a)
- —$(CH_2)_n$-pyridin-2,3 or 4-yl, or
- —$(CH_2)_n$-pyridin-2,3 or 4-yl substituted by
  - -lower alkyl,
  - —$(CH_2)_m$—O-lower alkyl,
  - —$(CH_2)_m$NR'R",
  - —$(CH_2)_m$morpholinyl,
  - —$(CH_2)_m$-pyrrolidin-1-yl,
  - —$(CH_2)_m$-piperidine-1-yl,
  - —$(CH_2)_m$-piperidine-1-yl substituted by hydroxy,
  - —$(CH_2)_m$—O—$(CH_2)_o$—$CF_3$,
  - —$(CH_2)_n$—O—$(CH_2)_m$-cycloalkyl,
  - —$(CH_2)_m$—O—$(CH_2)_o$—O-lower alkyl,
  - —$(CH_2)_m$—O—$(CH_2)_o$-2-oxo-pyrrolidin-1-yl,
  - —$(CH_2)_m$—O-tetrahydropyran-4-yl,
  - —$(CH_2)_m$—O—$(CH_2)_o$-morpholinyl,
  - -di-hydropyran-4-yl,
  - -tetra-hydropyran-4-yl,
  - -azetidin-1-yl, or
  - -azetidin-1-yl substituted by halogen, lower alkoxy or hydroxy; or b)
- —$(CH_2)_n$-piperidine-1-yl, or
- —$(CH_2)_n$-piperidine-1-yl substituted by one or two substituents selected from
  - -hydroxy, -hydroxy-lower alkyl, -lower alkyl and —$(CH_2)_m$—O-lower alkyl; or c)
- —$(CH_2)_n$-phenyl, or
- —$(CH_2)_n$-phenyl substituted by one or two substituents selected from
  - -halogen, -lower alkyl, -lower alkoxy and —$(CH_2)_n$—NR'R"; or d)
- -benzo[1.3]dioxol-5-yl;
- —$(CH_2)_n$-morpholinyl;
- —$(CH_2)_n$-tetrahydropyran-4-yl;
- —$(CH_2)_n$—O-lower alkyl;
- —$(CH_2)_n$-cycloalkyl;
- —$(CH_2)_n$—C(O)—NR'R";
- —$(CH_2)_n$-2-oxo-pyrrolidin-1-yl;
- —$(CH_2)_n$NR'R";

-2-oxa-5-aza-bicyclo[2.2.1]heptane-5-yl; or
-1-oxa-8-aza-spiro[4.5]decane-8-yl;

R' and R" are each independently selected from lower alkyl; —(CH$_2$)$_o$—O-lower alkyl; cycloalkyl; lower alkyl substituted by hydroxy; —(CH$_2$)$_n$—O-lower alkyl substituted by hydroxy; and cycloalkyl substituted by hydroxy;

n is 0, 1, 2 or 3;

m is 0 or 1; and o is 1 or 2;

or a pharmaceutically acceptable salt thereof.

3. The compound of claim 1, wherein R$^2$ is substituted —(CH$_2$)$_n$-pyridin-4-yl.

4. The compound of claim 3, wherein the substituents are selected from the group consisting of methyl, morpholinyl, azetidin-1-yl, 3-fluoro-azetidin-1-yl, 3-methoxy-azetidin-1-yl, 3-hydroxy-azetidin-1-yl and —O—(CH$_2$)$_2$-morpholinyl.

5. The compound of claim 4, which is selected from:

(+)-N-(7-[1,4]dioxan-2-yl-4-methoxy-benzothiazol-2-yl)-2-methyl-isonicotinamide,
(+)-N-(7-[1,4]dioxan-2-yl-4-methoxy-benzothiazol-2-yl)-2-morpholin-4-yl-isonicotinamide,
(+)-2-azetidin-1-yl-N-(7-[1,4]dioxan-2-yl-4-methoxy-benzothiazol-2-yl)-isonicotinamide,
(+)-N-(7-[1,4]dioxan-2-yl-4-methoxy-benzothiazol-2-yl)-2-(3-fluoro-azetidin-1-yl)-isonicotinamide,
(+)-N-(7-[1,4]dioxan-2-yl-4-methoxy-benzothiazol-2-yl)-2-(3-methoxy-azetidin-1-yl)-isonicotinamide,
(+)-N-(7-[1,4]dioxan-2-yl-4-methoxy-benzothiazol-2-yl)-2-(3-hydroxy-azetidin-1-yl)-isonicotinamide and
(+)-N-(7-[1,4]dioxan-2-yl-4-methoxy-benzothiazol-2-yl)-2-(2-morpholin-4-yl-ethoxy)-isonicotinamide.

6. The compound of claim 1, wherein R$^2$ is substituted —(CH$_2$)$_n$-pyridin-3-yl.

7. The compound of claim 6, wherein the substituent is methoxy.

8. The compound of claim 7, wherein the compound is (+)-N-(7-[1,4]dioxan-2-yl-4-methoxy-benzothiazol-2-yl)-5-methoxy-nicotinamide.

9. The compound of claim 1, wherein R$^2$ is substituted —(CH$_2$)$_n$-pyridin-2-yl.

10. The compound of claim 1, wherein R$^2$ is unsubstituted —(CH$_2$)$_n$-pyridin-2,3 or 4-yl.

11. The compound of claim 1, wherein R$^2$ is mono- or di-substituted —(CH$_2$)$_n$-phenyl.

12. The compound of claim 11, wherein the substituents are fluoro, mono- or di-methoxy or methyl.

13. The compound of claim 12, which is selected from (+)-N-(7-[1,4]dioxan-2-yl-4-methoxy-benzothiazol-2-yl)-4-fluoro-benzamide,
(+)-N-(7-[1,4]dioxan-2-yl-4-methoxy-benzothiazol-2-yl)-4-methoxy-benzamide,
(+)-N-(7-[1,4]dioxan-2-yl-4-methoxy-benzothiazol-2-yl)-4-methyl-benzamide, and
(+)-N-(7-[1,4]dioxan-2-yl-4-methoxy-benzothiazol-2-yl)-3-methoxy-benzamide.

14. The compound of claim 1, wherein R$^2$ is unsubstituted —(CH$_2$)$_n$-phenyl.

15. The compound of claim 1, wherein R$^2$ is benzo[1.3]dioxol-5-yl.

16. The compound of claim 15, wherein the compound is (+)-benzo[1,3]dioxole-5-carboxylic acid (7-[1,4]dioxan-2-yl-4-methoxy-benzothiazol-2-yl)-amide.

17. The compound of claim 1, wherein R$^2$ is selected from —(CH$_2$)$_n$-morpholinyl, —(CH$_2$)$_n$-tetrahydropyran-4-yl, —(CH$_2$)$_n$—O-lower alkyl, —(CH$_2$)$_n$-cycloalkyl, —(CH$_2$)$_n$—C(O)—NR'R", —(CH$_2$)$_n$-2-oxo-pyrrolidin-1-yl, —(CH$_2$)$_n$ NR'R", -2-oxa-5-aza-bicyclo[2.2.1]heptane-5-yl, and -1-oxa-8-aza-spiro[4.5]decane-8-yl.

18. A process for preparing a compound of formula I

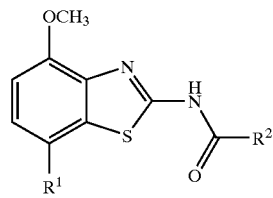

wherein

R$^1$ is selected from (RS)-[1,4]dioxan-2-yl-, (R)-[1,4]dioxan-2-yl-, and (S)-[1,4]dioxan-2-yl-;

R$^2$ is a)
—(CH$_2$)$_n$-pyridin-2,3 or 4-yl, or
—(CH$_2$)$_n$-pyridin-2,3 or 4-yl substituted by
-lower alkyl,
—(CH$_2$)$_m$—O-lower alkyl,
—(CH$_2$)$_m$NR'R",
—(CH$_2$)$_m$morpholinyl,
—(CH$_2$)$_m$-pyrrolidin-1-yl,
—(CH$_2$)$_m$-piperidine-1-yl,
—(CH$_2$)$_m$-piperidine-1-yl substituted by hydroxy,
—(CH$_2$)$_m$—O—(CH$_2$)$_o$—CF$_3$,
—(CH$_2$)$_n$—O—(CH$_2$)$_m$-cycloalkyl,
—(CH$_2$)$_m$—O—(CH$_2$)$_o$—O-lower alkyl,
—(CH$_2$)$_m$—O—(CH$_2$)$_o$-2-oxo-pyrrolidin-1-yl,
—(CH$_2$)$_m$—O-tetrahydropyran-4-yl,
—(CH$_2$)$_m$—O—(CH$_2$)$_o$-morpholinyl,
-di-hydropyran-4-yl,
-tetra-hydropyran-4-yl
-azetidin-1-yl, or
-azetidin-1-yl substituted by halogen, lower alkoxy or hydroxy; or b)
—(CH$_2$)$_n$-piperidine-1-yl, or
—(CH$_2$)$_n$-piperidine-1-yl substituted by one or two substituents selected from
-hydroxy, -hydroxy-lower alkyl, -lower alkyl and —(CH$_2$)$_m$—O-lower alkyl; or c)
—(CH$_2$)$_n$-phenyl, or
—(CH$_2$)$_n$-phenyl substituted by one or two substituents selected from
-halogen, -lower alkyl, -lower alkoxy and —(CH$_2$)$_n$—NR'R"; or d)
-benzo[1.3]dioxol-5-yl;
—(CH$_2$)$_n$-morpholinyl;
—(CH$_2$)$_n$-tetrahydropyran-4-yl;
—(CH$_2$)$_n$—O-lower alkyl;
—(CH$_2$)$_n$-cycloalkyl;
—(CH$_2$)$_n$—C(O)—NR'R";
—(CH$_2$)$_n$-2-oxo-pyrrolidin-1-yl;
—(CH$_2$)$_n$NR'R";
-2-oxa-5-aza-bicyclo[2.2.1]heptane-5-yl; or
-1-oxa-8-aza-spiro[4.5]decane-8-yl;

R' and R" are each independently selected from lower alkyl; —(CH$_2$)$_o$—O-lower alkyl; cycloalkyl; lower alkyl substituted by one or more substituents selected from hydroxy and lower alkyl; —(CH$_2$)$_o$—O-lower alkyl substituted by one or more substituents selected from hydroxy and lower alkyl; and cycloalkyl substituted by one or more substituents selected from hydroxy and lower alkyl;

n is 0, 1, 2 or 3;

m is 0 or 1; and o is 1 or 2;

or a pharmaceutically acceptable salt thereof, which process comprises a) reacting a compound of formula 5

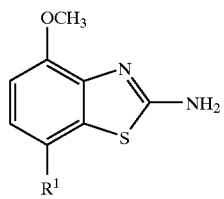
(5)

with a compound of formula

ClC(O)R$^2$/base (6)

or with a compound of formula

HOC(O)R$^2$/HATU/base (7)

to produce a compound of formula I

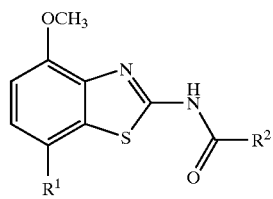
I wherein R$^1$ and R$^2$ as defined above.

19. A process for preparing a compound of formula I

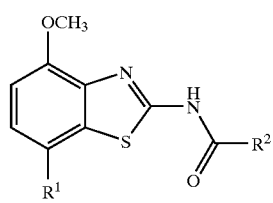
I wherein

R$^1$ is selected from (RS)-[1,4]dioxan-2-yl-, (R)-[1,4]dioxan-2-yl-, and (S)-[1,4]dioxan-2-yl-;

R$^2$ is a)
—(CH$_4$)$_n$-pyridin-2,3 or 4-yl, or
—(CH$_2$)$_n$-pyridin-2,3 or 4-yl substituted by
-lower alkyl,
—(CH$_2$)$_m$—O-lower alkyl,
—(CH$_2$)$_m$NR'R",
—(CH$_2$)$_m$morpholinyl,
—(CH$_2$)$_m$-pyrrolidin-1-yl,
—(CH$_2$)$_m$-piperidine-1-yl,
—(CH$_2$)$_m$-piperidine-1-yl substituted by hydroxy,
—(CH$_2$)$_m$—O—(CH$_2$)$_o$—CF$_3$,
—(CH$_2$)$_n$—O—(CH$_2$)$_m$-cycloalkyl,
—(CH$_2$)$_m$—O—(CH$_2$)$_o$—O-lower alkyl,
—(CH$_2$)$_m$—O—(CH$_2$)$_o$-2-oxo-pyrrolidin-1-yl,
—(CH$_2$)$_m$—O-tetrahydropyran-4-yl,
—(CH$_2$)$_m$—O—(CH$_2$)$_o$-morpholinyl,
-di-hydropyran-4-yl,
-tetra-hydropyran-4-yl
-azetidin-1-yl, or
-azetidin-1-yl substituted by halogen, lower alkoxy or hydroxy, or b)
—(CH$_2$)$_n$-piperidine-1-yl, or
—(CH$_2$)$_n$-piperidine-1-yl substituted by one or two substituents selected from
-hydroxy, -hydroxy-lower alkyl, -lower alkyl and —(CH$_2$)$_m$—O-lower alkyl; or c)
—(CH$_2$)$_n$-phenyl, or
—(CH$_2$)$_n$-phenyl substituted by one or two substituents selected from
-halogen, -lower alkyl, -lower alkoxy and —(CH$_2$)$_n$—NR'R"; or d)
-benzo[1.3]dioxol-5-yl;
—(CH$_2$)$_n$-morpholinyl;
—(CH$_2$)$_n$-tetrahydropyran-4-yl;
—(CH$_2$)$_n$—O-lower alkyl;
—(CH$_2$)$_n$-cycloalkyl;
—(CH$_2$)$_n$—C(O)—NR'R";
—(CH$_2$)$_n$-2-oxo-pyrrolidin-1-yl;
—(CH$_2$)$_n$NR'R";
-2-oxa-5-aza-bicyclo[2.2.1]heptane-5-yl; or
-1-oxa-8-aza-spiro[4.5]decane-8-yl;

R' and R" are each independently selected from lower alkyl; —(CH$_2$)$_o$—O-lower alkyl; cycloalkyl; lower alkyl substituted by one or more substituents selected from hydroxy and lower alkyl; —(CH$_2$)$_o$—O-lower alkyl substituted by one or more substituents selected from hydroxy and lower alkyl; and cycloalkyl substituted by one or more substituents selected from hydroxy and lower alkyl;

n is 0, 1, 2 or 3;

m is 0 or 1; and o is 1 or 2;

or a pharmaceutically acceptable salt thereof, which process comprises reacting a compound of formula 8

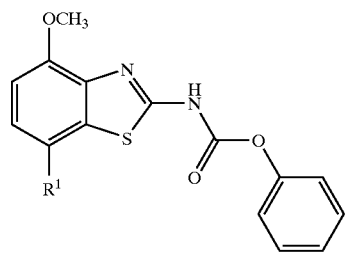
(8)

with a compound of formula

HR$^2$/base (9)

to produce a compound of formula I

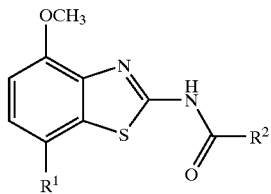

wherein $R^1$ and $R^2$ as defined above.

20. A process for preparing a compound of formula I

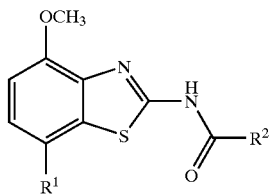

wherein
$R^1$ is selected from (RS)-[1,4]dioxan-2-yl-, (R)-[1,4]dioxan-2-yl-, and (S)-[1,4]dioxan-2-yl-;
$R^2$ is
a)
—$(CH_2)_n$-pyridin-2,3 or 4-yl, or
—$(CH_2)_n$-pyridin-2,3 or 4-yl substituted by
-lower alkyl,
—$(CH_3)_m$—O-lower alkyl,
—$(CH_2)_m$NR'R",
—$(CH_2)_m$morpholinyl,
—$(CH_2)_m$-pyrrolidin-1-yl,
—$(CH_2)_m$-piperidine-1-yl,
—$(CH_2)_m$-piperidine-1-yl substituted by hydroxy,
—$(CH_2)_m$—O—$(CH_2)_o$—$CF_3$,
—$(CH_2)_n$—O—$(CH_2)_m$-cycloalkyl,
—$(CH_2)_m$—O—$(CH_2)_o$—O-lower alkyl,
—$(CH_2)_m$—O—$(CH_2)_o$-2-oxo-pyrrolidin-1-yl,
—$(CH_2)_m$—O-tetrahydropyran-4-yl,
—$(CH_2)_m$—O—$(CH_2)_o$-morpholinyl,
-di-hydropyran-4-yl,
-tetra-hydropyran-4-yl
-azetidin-1-yl, or
-azetidin-1-yl substituted by halogen, lower alkoxy or hydroxy; or
b)
—$(CH_2)_n$-piperidine-1-yl, or
—$(CH_2)_n$-piperidine-1-yl substituted by one or two substituents selected from
-hydroxy, -hydroxy-lower allyl, -lower alkyl and —$(CH_2)_m$—O-lower alkyl; or
c)
—$(CH_2)_n$-phenyl, or
—$(CH_2)_n$-phenyl substituted by one or two substituents selected from
-halogen, -lower alkyl, -lower alkoxy and —$(CH_2)_n$—NR'R"; or
d)
-benzo[1.3]dioxol-5-yl;
—$(CH_2)_n$-morpholinyl;
—$(CH_2)_n$-tetrahydropyran-4-yl;
—$(CH_2)_n$—O-lower alkyl;
—$(CH_2)_n$-cycloalkyl;
—$(CH_2)_n$—C(O)—NR'R";
—$(CH_2)_n$-2-oxo-pyrrolidin-1-yl;
—$(CH_2)_n$NR'R";
-2-oxa-5-aza-bicyclo[2.2.1]heptane-5-yl; or
-1-oxa-8-aza-spiro[4.5]decane-8-yl;
R' and R" are each independently selected from lower alkyl; —$(CH_2)_o$—O-lower alkyl; cycloalkyl; lower alkyl substituted by one or more substituents selected from hydroxy and lower alkyl; —$(CH_2)_o$—O-lower alkyl substituted by one or more substituents selected from hydroxy and lower alkyl; and cycloalkyl substituted by one or more substituents selected from hydroxy or lower alkyl;
n is 0, 1, 2 or 3;
m is 0 or 1; and
o is 1 or 2;
or a pharmaceutically acceptable salt thereof, which process comprises separating a racemic compound of formula I into its (R)- and (S)-enantiomers.

21. The process of claim 18 further comprising converting the compound of formula I obtained into its pharmaceutically acceptable salt.

22. The process of claim 19 further comprising converting the compound of formula I obtained into its pharmaceutically acceptable salt.

23. The process of claim 20 further comprising converting the compound of formula I obtained into its pharmaceutically acceptable salt.

24. A pharmaceutical composition which comprises a compound of formula I

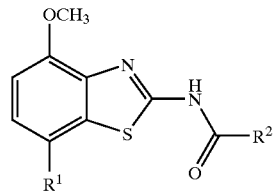

wherein
$R^1$ is selected from (RS)-1,4]dioxan-2-yl-, (R)-[1,4]dioxan-2-yl-, and (S)-[1,4]dioxan-2-yl-;
$R^2$ is
a)
—$(CH_2)_n$-pyridin-2,3 or 4-yl, or
—$(CH_2)_n$-pyridin-2,3 or 4-yl substituted by
-lower alkyl,
—$(CH_2)_m$—O-lower alkyl,
—$(CH_2)_m$NR'R",
—$(CH_2)_m$morpholinyl,
—$(CH_2)_m$-pyrrolidin-1-yl,
—$(CH_2)_m$-piperidine-1-yl,
—$(CH_2)_m$-piperidine-1-yl substituted by hydroxy,
—$(CH_2)_m$—O—$(CH_2)_o$—$CF_3$,
—$(CH_2)_n$—O—$(CH_2)_m$-cycloalkyl,
—$(CH_2)_m$—O—$(CH_2)_o$—O-lower alkyl,
—$(CH_2)_m$—O—$(CH_2)_o$-2-oxo-pyrrolidin-1-yl,
—$(CH_2)_m$—O-tetrahydropyran-4-yl,
—$(CH_2)_m$—O—$(CH_2)_o$-morpholinyl, -di-hydropyran-4-yl,
-tetra-hydropyran-4-yl
-azetidin-1-yl, or
-azetidin-1-yl substituted by halogen, lower alkoxy or hydroxy, or b)
—(CH$_2$)$_n$-piperidine-1-yl, or
—(CH$_2$)$_n$-piperidine-1-yl substituted by one or two substituents selected from
-hydroxy, -hydroxy-lower alkyl, -lower alkyl and —(CH$_2$)$_m$—O-lower alkyl; or c)
—(CH$_2$)$_n$-phenyl, or
—(CH$_2$)$_n$-phenyl substituted by one or two substituents selected from
-halogen, -lower alkyl, -lower alkoxy and —(CH$_2$)$_n$—NR'R"; or d)
-benzo[1.3]dioxol-5-yl;
—(CH$_2$)$_n$-morpholinyl;
—(CH$_2$)$_n$-tetrahydropyran-4-yl;
—(CH$_2$)$_n$—O-lower alkyl;
—(CH$_2$)$_n$-cycloalkyl;
—(CH$_2$)$_n$—C(O)—NR'R";
—(CH$_2$)$_n$-2-oxo-pyrrolidin-1-yl;
—(CH$_2$)$_n$NR'R";
-2-oxa-5-aza-bicyclo[2.2.1]heptane-5-yl; or
-1-oxa-8-aza-spiro[4.5]decane-8-yl;

R' and R" are each independently selected from lower alkyl; —(CH$_2$)$_o$—O-lower alkyl; cycloalkyl; lower alkyl substituted by one or more substituents selected from hydroxy and lower alkyl; —(CH$_2$)$_o$—O-lower alkyl substituted by one or more substituents selected from hydroxy and lower alkyl, and cycloalkyl substituted by one or more substituents selected from hydroxy or lower alkyl;

n is 0, 1, 2 or 3;
m is 0 or 1; and
o is 1 or 2;
or a pharmaceutically acceptable salt thereof,
and a pharmaceutically acceptable excipient.

25. A method of treating a disease based on adenosine A$_{2a}$ receptor activity comprising administering to a patient in need of such treatment a therapeutically effective amount of at least one compound of formula I

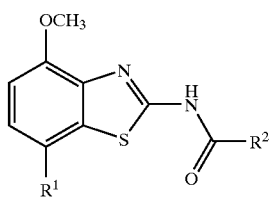

I wherein
R$^1$ is selected from (RS)-[1,4]dioxan-2-yl-, (R)-[1,4]dioxan-2-yl-, and (S)-[1,4]dioxan-2-yl-;

R$^2$ is
a)
—(CH$_2$)$_n$-pyridin-2,3 or 4-yl, or
—(CH$_2$)$_n$-pyridin-2,3 or 4-yl substituted by
-lower alkyl
—(CH$_2$)$_m$—O-lower alkyl,
—(CH$_2$)$_m$NR'R",
—(CH$_2$)$_m$morpholinyl,
—(CH$_2$)$_m$-pyrrolidin-1-yl,
—(CH$_2$)$_m$-piperidine-1-yl,
—(CH$_2$)$_m$-piperidine-1-yl substituted by hydroxy,
—(CH$_2$)$_m$—O—(CH$_2$)$_o$—CF$_3$,
—(CH$_2$)$_n$—O—(CH$_2$)$_m$-cycloalkyl,
—(CH$_2$)$_m$—O—(CH$_2$)$_o$—O-lower alkyl,
—(CH$_2$)$_m$—O—(CH$_2$)$_o$-2-oxo-pyrrolidin-1-yl,
—(CH$_2$)$_m$—O-tetrahydropyran-4-yl,
—(CH$_2$)$_m$—O—(CH$_2$)$_o$-morpholinyl,
-di-hydropyran-4-yl,
-tetra-hydropyran-4-yl
-azetidin-1-yl, or
-azetidin-1-yl substituted by halogen, lower alkoxy or hydroxy; or b)
—(CH$_2$)$_n$-piperidine-1-yl, or
—(CH$_2$)$_n$-piperidine-1-yl substituted by one or two substituents selected from
-hydroxy, -hydroxy-lower alkyl, -lower alkyl and —(CH$_2$)$_m$—O-lower alkyl; or c)
—(CH$_2$)$_n$-phenyl, or
—(CH$_2$)$_n$-phenyl substituted by one or two substituents selected from
-halogen, -lower alkyl, -lower alkoxy and —(CH$_2$)$_n$—NR'R"; or d)
-benzo[1.3]dioxol-5-yl;
—(CH$_2$)$_n$-morpholinyl;
—(CH$_2$)$_n$-tetrahydropyran-4-yl;
—(CH$_2$)$_n$—O-lower alkyl;
—(CH$_2$)$_n$-cycloalkyl;
—(CH$_2$)$_n$—C(O)—NR'R";
—(CH$_2$)$_n$-2-oxo-pyrrolidin-1-yl;
—(CH$_2$)$_n$NR'R";
-2-oxa-5-aza-bicyclo[2.2.1]heptane-5-yl; or
-1-oxa-8-aza-spiro[4.5]decane-8-yl;

R' and R" are each independently selected from lower alkyl; —(CH$_2$)$_o$—O-lower alkyl; cycloalkyl; lower alkyl substituted by one or more substituents selected from hydroxy and lower alkyl; —(CH$_2$)$_o$—O-lower alkyl substituted by one or more substituents selected from hydroxy and lower alkyl; and cycloalkyl substituted by one or more substituents selected from hydroxy or lower alkyl;

n is 0, 1, 2 or 3;
m is 0 or 1; and
o is 1 or 2;
or a pharmaceutically acceptable salt thereof.

* * * * *